United States Patent
Montell et al.

(10) Patent No.: US 11,385,223 B2
(45) Date of Patent: Jul. 12, 2022

(54) ANASTASIS BIOSENSOR

(71) Applicant: THE JOHNS HOPKINS UNIVERSITY, Baltimore, MD (US)

(72) Inventors: Denise Montell, Lutherville, MD (US); Ho Lam Tang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 93 days.

(21) Appl. No.: 16/248,157

(22) Filed: Jan. 15, 2019

(65) Prior Publication Data

US 2019/0376954 A1  Dec. 12, 2019

Related U.S. Application Data

(62) Division of application No. 14/383,156, filed as application No. PCT/US2013/029594 on Mar. 7, 2013, now abandoned.

(60) Provisional application No. 61/607,799, filed on Mar. 7, 2012.

(51) Int. Cl.

| | |
|---|---|
| C12N 5/02 | (2006.01) |
| C12N 15/63 | (2006.01) |
| C12N 15/79 | (2006.01) |
| C07H 21/04 | (2006.01) |
| G01N 33/50 | (2006.01) |
| G01N 33/68 | (2006.01) |
| G01N 33/58 | (2006.01) |
| A01K 67/027 | (2006.01) |

(52) U.S. Cl.
CPC ..... *G01N 33/5091* (2013.01); *A01K 67/0275* (2013.01); *G01N 33/582* (2013.01); *G01N 33/6872* (2013.01); *A01K 2227/105* (2013.01); *A01K 2267/0393* (2013.01); *G01N 2510/00* (2013.01)

(58) Field of Classification Search
CPC ...... C12N 15/63; C12N 15/79; G01N 33/582; G01N 33/5091; C07H 21/04
See application file for complete search history.

(56) References Cited

U.S. PATENT DOCUMENTS

| | | | |
|---|---|---|---|
| 7,354,735 B2 | 4/2008 | Chang et al. | |
| 2007/0231865 A1 | 10/2007 | Spears et al. | |
| 2009/0131270 A1 | 5/2009 | Taylor et al. | |

FOREIGN PATENT DOCUMENTS

| | | | |
|---|---|---|---|
| WO | 1999025840 A1 | 5/1999 | |
| WO | 2000073802 A1 | 7/2000 | |
| WO | 2001/075453 A2 | 10/2001 | |
| WO | 2006/017751 A2 | 2/2006 | |

OTHER PUBLICATIONS

Rossner et al., 2009, US 20090298089 A1.*
Hay et al., 2002, US 20020132327 A1.*
Aitken, et al., Apoptosis in the germ line. Reproduction 141, 139-150. (2011).
Arama, et al., Caspase activity and a specific cytochrome Care required for sperm differentiation in *Drosophila*. Dev Cell 4, 687-697. (2003).
Bloom, Induced chromosomal aberrations: biological and clinical significance. J Pediatr 81, 1-8. (1972).
Boffetta, et al., Alcohol and cancer. Lancet Oncol 7, 149-156. (2006).
Capy, et al., Stress and transposable elements: co-evolution or useful parasites? Heredity 85, 101-106. (2000).
Chabaud, et al., Apoptosis modulation as a promising target for treatment of systemic sclerosis. Int J Rheumatol 2011, 495792. (2011).
Chipuk, et al., The BCL-2 family reunion. Mol Cell 37, 299-310. (2010).
Cifone, et al., Correlation of patterns of anchorage-independent growth with in vivo behavior of cells from a murine fibrosarcoma. Proc Natl Acad Sci USA 77, 1039-1043. (1980).
Coleman, et al., Membrane blebbing during apoptosis results from caspase-mediated activation of ROCK I. Nat Cell Biol 3, 339-345. (2001).
Drummond-Barbosa, et al., Stem cells and their progeny respond to nutritional changes during *Drosophila* bogenesis. Dev Biol 231, 265-278. (2001).
Enari, et al., A caspase-activated DNase that degrades DNA during apoptosis, and its inhibitor ICAD. Nature 391, 43-50. (1998).
Fenech, Cytokinesis-block micronucleus cytome assay. Nat Protoc 2, 1084-1104. (2007).
Fischer, et al., Apoptosis-based therapies and drug targets. Cell Death Differ 12 (Suppl 1), 942-961. (2005).
Fu, et al., Balancing repair and tolerance of DNA damage caused by alkylating agents. Nat Rev Cancer 12, 104-120. (2012).
Fuchs, et al., Programmed cell death in animal development and disease. Cell 147, 742-758. (2011).
German, Cytological evidence for crossing-over in vitro in human lymphoid cells. Science 144, 298-301. (1964).
Goldin, et al., Apoptotic bodies in a murine model of alcoholic liver disease: reversibility of ethanol-induced changes. J Pathol 171, 73-76. (1993).
Gordon, et al., Causes and consequences of aneuploidy in cancer. Nat Rev Genet 13, 189-203. (2012).

(Continued)

*Primary Examiner* — Shin Lin Chen
(74) *Attorney, Agent, or Firm* — Johns Hopkins Technology Ventures

(57) ABSTRACT

The present invention relates to the field of anastasis, i.e., the process of reversal of apoptosis. More specifically, the present invention provides methods and compositions useful for studying anastasis. In one embodiment, the present invention provides an in vivo biosensor comprising (a) a transcription factor complex comprising the Gal4 transcription factor linked to an enzyme cleavable linker, wherein the transcription factor complex is tethered to the plasma membrane via a transmembrane domain; and (b) a reporter system comprising (1) a first nucleic acid encoding flippase operably linked to the upstream activating sequence that binds Gal4; and (2) a second nucleic acid comprising an FRT-flanked stop codon cassette separating a constitutive promoter and a fluorescent protein open reading frame.

2 Claims, 23 Drawing Sheets

Specification includes a Sequence Listing.

(56) References Cited

OTHER PUBLICATIONS

Gordon, et al., DNA damage and repair in light-induced photoreceptor degeneration. Invest Ophthalmol Visual Sci 43, 3511-3521. (2002).
Green, et al., The pathophysiology of mitochondrial cell death. Science 305, 626-629. (2004).
Guicciardi, et al., Apoptosis as a mechanism for liver disease progression. Semin Liver Dis 30, 402-410. (2010).
Hu, et al., Molecular cloning and expression of a functional anti-inflammatory protein, Sj16, of Schistosoma japonicum. Int J Parasitol 39, 191-200. (2009).
Iravanian, et al., Functional reentry in cultured monolayers of neonatal rat cardiac cells. Am J Physiol Heart Circ Physiol 285, H449-H456. (2003).
Jacobson, et al., Programmed cell death in animal development. Cell 88, 347-354. (1997).
Jaiswal, et al., Long-term multiple color imaging of live cells using Quantum Dot bioconjugates. Nat Biotechnol 21, 47-51. (2003).
Jiang, et al., An active DNA transposon family in rice. Nature 421, 163-167. (2003).
Johnstone, et al., Apoptosis: a link between cancer genetics and chemotherapy. Cell 108, 153-164. (2002).
Kerr, et al., Apoptosis: a basic biological phenomenon with wide-ranging implications in tissue kinetics. Br J Cancer 26, 239-257. (1972).
Kroemer, et al., Classification of cell death: recommendations of the Nomenclature Committee on Cell Death 2009. Cell Death Differ 16, 3-11. (2009).
Lazebnik, et al., Cleavage of poly(ADP-ribose) polymerase by a proteinase with properties like ICE. Nature 371, 346-347. (1994).
Li, et al., Endo nuclease G is an apoptotic DNase when released from mitochondria. Nature 412, 95-99. (2001).
Liu, et al., Chromosome catastrophes involve replication mechanisms generating complex genomic rearrangements. Cell 146, 889-903. (2011).
Liu, et al., DFF, a heterodimeric protein that functions downstream of caspase-3 to trigger DNA fragmentation during apoptosis. Cell 89, 175-184. (1997).
Logue, et al., Expression, purification and use of recombinant annexin V for the detection of apoptotic cells. Nat Protoc 4, 1383-1395. (2009).
Luthi, et al., The CASBAH: a searchable database of caspase substrates. Cell Death Differ 14, 641-650. (2007).
MacLeod, et al., Cytogenetic harvesting of commonly used tumor cell lines. Nat Protoc 2, 372-3 82. (2007).
Masters, HeLa cells 50 years on: the good, the bad and the ugly. Nat Rev Cancer2, 315-319. (2002).
McClintock, The significance of responses of the genome to challenge. Science 226, 792-801. (1984).
McKechnie, et al., Recovery of the rabbit retina after light damage (preliminary observations). Albrecht Von Graefes Arch Klin Exp Ophthalmol 212,271-283. (1980).
McKillop, et al., Alcohol and liver cancer. Alcohol 35, 195-203. (2005).
Milligan, et al., Thephosphatidylinositol transfer protein domain of *Drosophila* retinal degeneration B protein is essential for photoreceptor cell survival and recovery from light stimulation. J Cell Biol 139,351-363. (1997).
Narula, et al., Mechanisms ofdisease: apoptosis in heart failure-seeing hope in death. Nat Clin Pract Cardiovasc Med 3,681-688. (2006).
Narula, et al., Apoptosis in heart failure: release of cytochrome c frommitochondria and activation of caspase-3 in human cardiomyopathy. Proc Natl Acad Sci USA 96, 8144-8149. (1999).
Olive, et al., The comet assay: a method to measure DNA damage in individual cells. Nat Protoc 1, 23-29.(2006).
Reed, et al., Postmitochondrial regulation of apoptosisduring heart failure. Proc Natl Acad Sci USA 96, 7614-7616. (1999).
Riedl, et al., Molecular mechanisms of caspase regulation duringapoptosis. Nat Rev Mol Cell Biol 5, 897-907. (2004).
Rosenberg, Evolving responsively: adaptive mutation. Nat Rev Genet 2, 504-515. (2001).
Ross, Induction of cell death by radiotherapy. Endocr Related Cancer 6, 41-44. (1999).
Rubin, Cell-cell contact interactions conditionally determine suppression and selection of the neoplastic phenotype. Proc Natl Acad Sci USA 205, 6215-6221. (2008).
Salinas, et al., Stress-induced gem1 cellapoptosis is by a p53 independent pathway in Caenorhabditis elegans. Cell Death Differ 13,2 129-2139. (2006).
Albeck, J., et al., "Quantitative analysis of pathways controlling extrinsic apoptosis in single cells" Molecular Cell 10, pp. 11-25, Apr. 11, 2008.
Office Action dated Feb. 10, 2017 in related U.S. Appl. No. 14/383,156.
Response to Office Action dated Feb. 10, 2017 in related U.S. Appl. No. 14/383,156.
Final Office Action dated Oct. 12, 2018 in related U.S. Appl. No. 14/383,156.
Office Action dated Jun. 22, 2016 in related U.S. Appl. No. 14/383,156.
Response to Final Office Action dated Jun. 22, 2016 in related U.S. Appl. No. 14/383,156.
Office Action dated Jan. 30, 2018 in related U.S. Appl. No. 14/383,156.
Response to Office Action dated Jan. 30, 2018 in related U.S. Appl. No. 14/383,156.
Extended European Search Report dated May 18, 2020 for related EPO application 17870867.3.
Sawicki, et al., On the recovery of transcription after inhibition by actinomycin D. J Cell Biol 55, 299-309. (1972).
Stephens, et al., Massive genomic rearrangement acquired in a single catastrophic event during cancer development. Cell 144, 27-40. (2011).
Stratton, et al., The cancer genome. Nature 458, 719-724. (2009).
Susin, et al., Molecular characterization of mitochondrial apoptosis-inducing factor. Nature 397, 441-446. (1999).
Takemoto, et al., Spatio-temporal activation of caspase revealed by indicator that is insensitive to environmental effects. J Cell Biol 160, 235-243. (2003).
Talanian, et al., Substrate specificities of caspase family proteases. J Biol Chem 272, 9677-9682. (1997).
Tang, et al., Reversibility of apoptosis in cancer cells. Br J Cancer 100, 118-122. (2009).
Taylor, et al., Apoptosis: controlled demolition at the cellular level. Nat Rev Mol Cell Biol 9, 231-241. (2008).
Wang, et al., PARP is important for genomic stability but dispensable in apoptosis. Genes Dev 11, 2347-2358. (1997).
Zurlo, et al., Characterization of a primary hepatocyte culture system for toxicological studies. In Vitro Cell Dev Biol Anim 32, 211-220. (1996).
Evans, et al., G-TRACE: rapid Gal4-based cell lineage analysis in *Drosophila*. Nat Methods 6, 603-605. (2009).
Bardet, et al., A fluorescent reporter of caspase activity for live imaging. Proc Natl Acad Sci U S A 105, 13901-5 (2008).
Ditzel, et al., Degradation of DIAP1 by the N-end rule pathway is essential for regulating apoptosis. Nat Cell Biol 5, 467-473. (2003).
Badea, et al., A noninvasive genetic/pharmacologic strategy for visualizing cell morphology and clonal relationships in the mouse. J Neurosci 15, 2313-2322 (2003).
Steiner, et al., An in vivo assay for the identification of target proteases which cleave membrane-associated substrates. FEBS Lett 17, 245-249. (1999).
Tang, et al., Cell survival, DNA damage, and oncogenic transformation following a transient and reversible apoptotic response. Mol Biol Cell 23, 2240-2251. (2012).
Goyal, et al., Induction of apoptosis by *Drosophila* reaper, hid and grim through inhibition of IAP function. EMBO J 19, 589-97 (2000).
Garg, et al., Apoptosis and heart failure: clinical relevance and therapeutic target. JMol Cell Cardiol 38, 73-9 (2005).

(56) References Cited

OTHER PUBLICATIONS

Venkatachalam, et al., Motor deficit in a *Drosophila* model of mucolipidosis type IV due to defective clearance of apoptotic cells. Cell 135, 838-51 (2008).
Yi, et al., Rapid cold-hardening protects *Drosophila melanogaster* from cold-induced apoptosis. Apoptosis 12, 1183-93 (2007).
Ranganathan, Matter of Life or Death. Science 299, 1677-1679 (2003).
Li, et al., Selective anticancer strategies via intervention of the death pathways relevant to cell transformation. Cell Death Differ 15, 1197-210 (2008).
Abbott, Ultrastructure of cell death in gamma- or X-irradiated imaginal wing discs of *Drosophila*. Radiat Res 96, 611-27 (1983).
Pritchett, et al., Cracking open cell death in the *Drosophila* ovary. Apoptosis 14, 969-79 (2009).
Kitamoto, Conditional modification of behavior in *Drosophila* by targeted expression of a temperature-sensitive shibire allele in defined neurons. JNeurobiol 47, 81-92 (2001).
Silva, et al., ATM is required for telomere maintenance and chromosome stability during *Drosophila* development. Curr Biol 14, 1341-7 (2004).
Mollereau, et al., Photoreceptor differentiation in *Drosophila*: from immature neurons to functional photoreceptors. Dev Dyn 232, 585-92 (2005).
Gambis, et al., Two-color in vivo imaging of photoreceptor apoptosis and development in *Drosophila*. Dev Biol 351, 128-34 (2011).
Pichaud, et al., A new visualization approach for identifying mutations that affect differentiation and organization of the *Drosophila* ommatidia. Development 128, 815-26 (2001).
Geisbrecht, et al., A role for *Drosophila* IAP1-mediated caspase inhibition in Racdependent cell migration. Cell 118, 111-25 (2004).
Helfer, et al., Caspase-8 promotes cell motility and calpain activity under nonapoptotic conditions. Cancer Res 66, 4273-8 (2006).
Malhi, et al., Hepatocyte death: a clear and present danger. Physiol Rev 90, 1165-94 (2010).
Lin, et al., Mitochondrial dysfunction and oxidative stress in neurodegenerative diseases. Nature 443, 787-95 (2006).
Yang, et al., Excessive Dpp signaling induces cardial apoptosis through dTAK1 and dJNK during late embryogenesis of *Drosophila*. JBiomed Sci 18, 85 (2011).
Tain, et al., *Drosophila* HtrA2 is dispensable for apoptosis but acts downstream of PINK 1 independently from Parkin. Cell Death Differ 16, 1118-25 (2009).
Stoller, et al., Cre reporter mouse expressing a nuclear localized fusion of GFP and betagalactosidase reveals new derivatives of Pax3-expressing precursors. Genesis 46, 200-4 (2008).
Cordeiro, et al., Imaging multiple phases of neurodegeneration: a novel approach to assessing cell death in vivo. Cell Death Dis 1, e3 (2010).
Youssef, et al., Retinal light toxicity. Eye (Loud) 25, 1-14 (2011).
Saito, et al., Involvement of ceramide in ethanol-induced apoptotic neurodegeneration in the neonatal mouse brain. JNeurochem 115, 168-77 (2010).
Waldmeier, et al., Interrupting apoptosis in neurodegenerative disease: potential for effective therapy? Drug Discov Today 9, 210-218. (2004).

\* cited by examiner

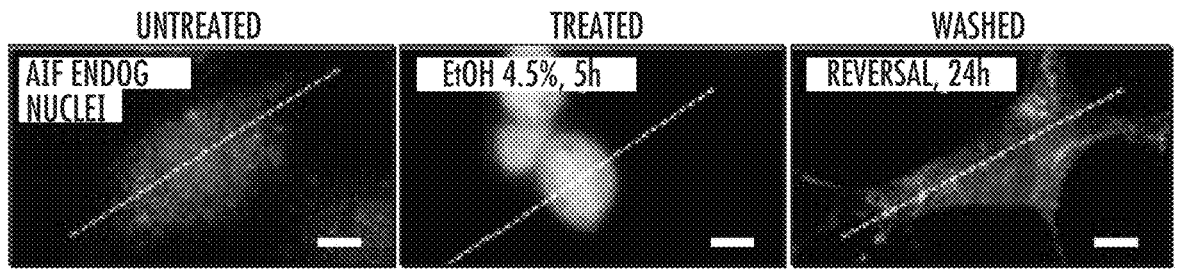
FIG. 12A
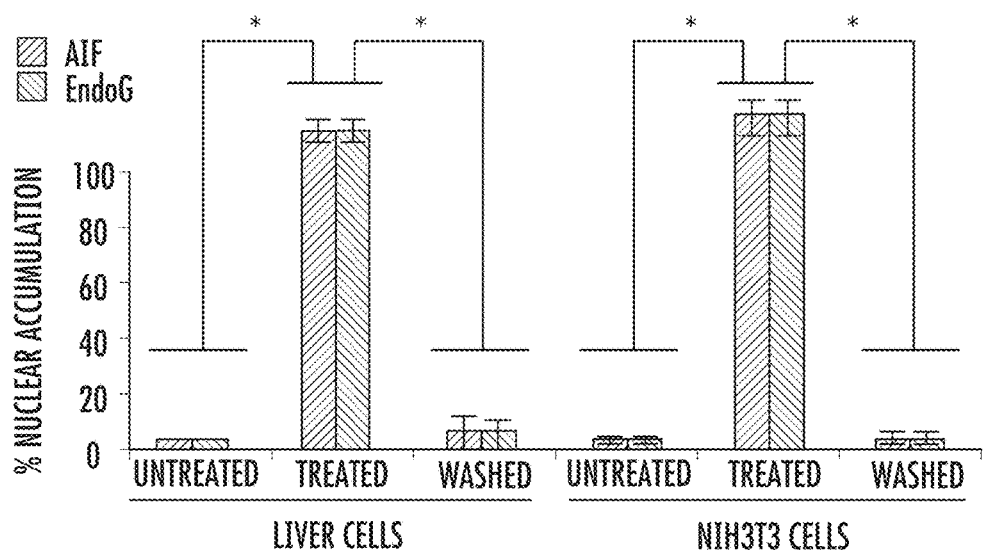
FIG. 12B
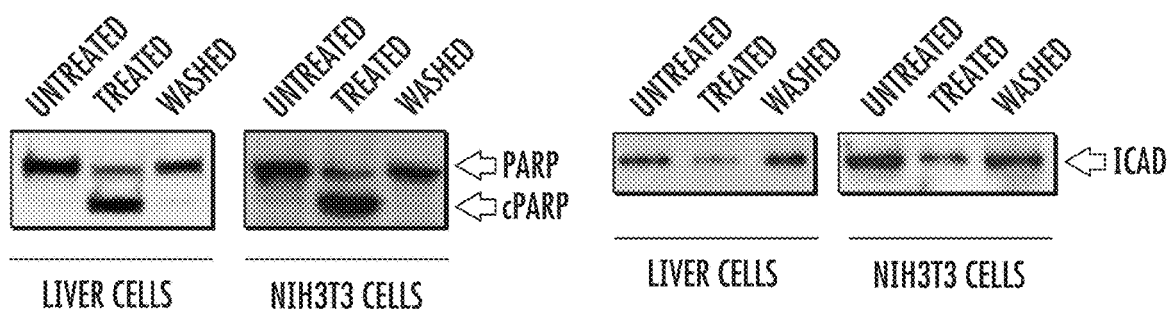
FIG. 12C
FIG. 12D

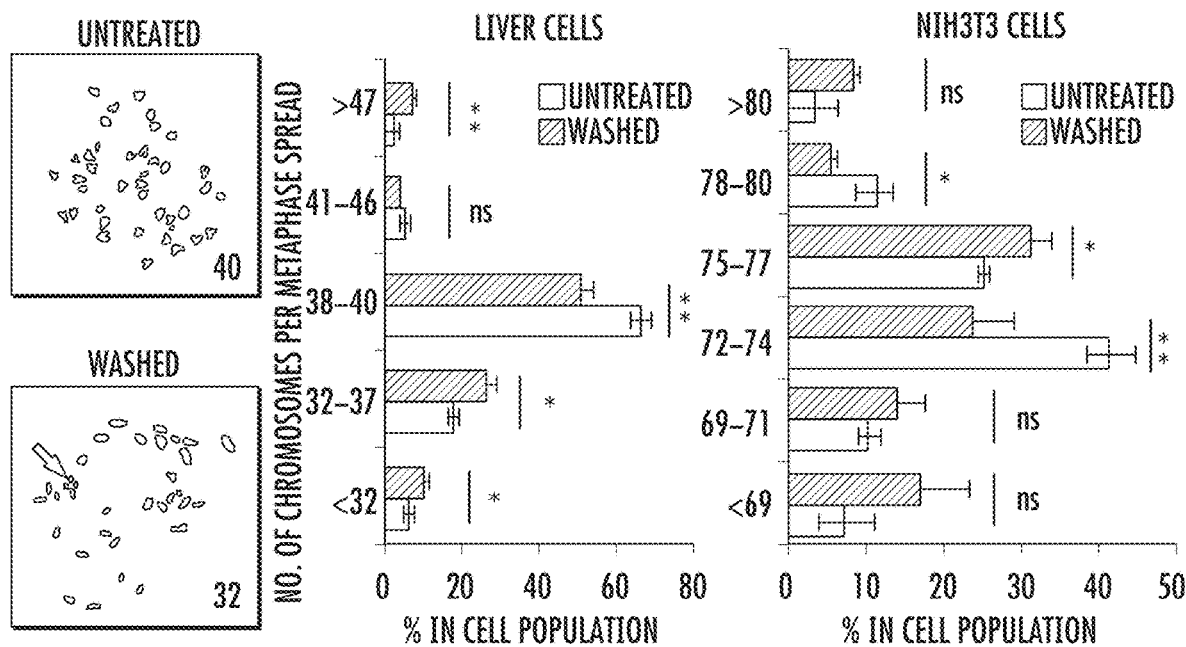
FIG. 13A
FIG. 13B
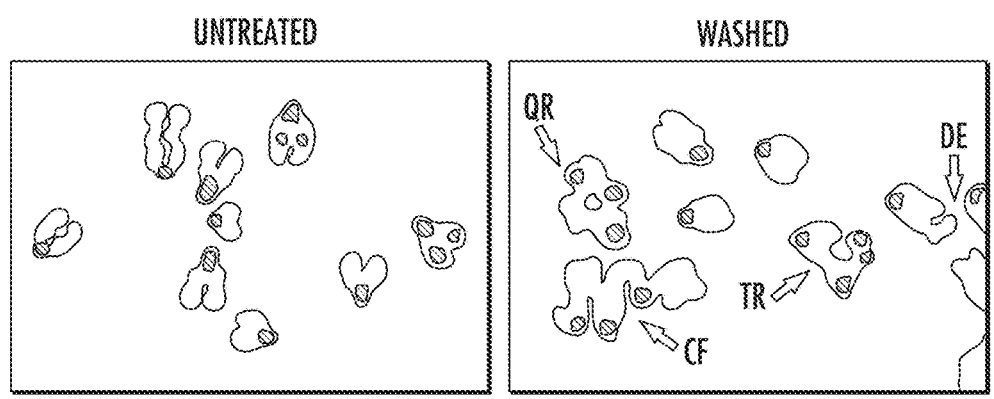
FIG. 13C
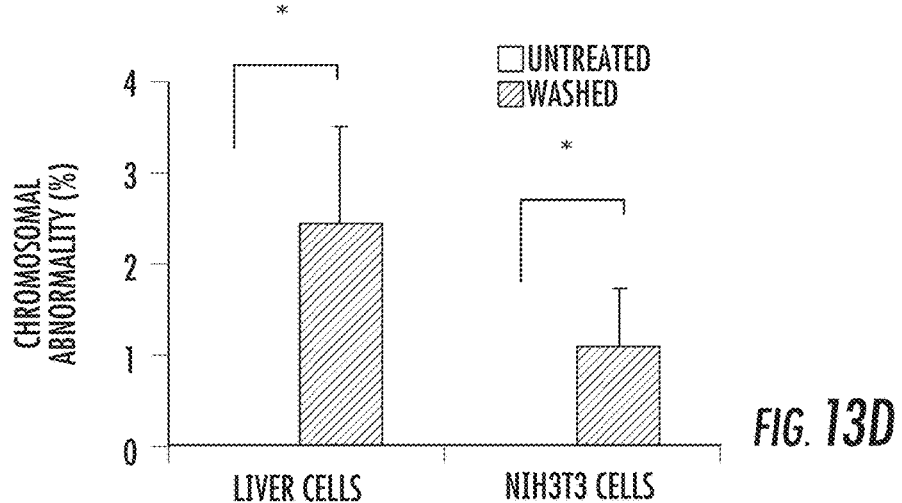
FIG. 13D

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
```

```
<220> FEATURE:
<223> OTHER INFORMATION: Bcl2 forward primer

<400> SEQUENCE: 1
cctgtggatg actgagtacc                                              20

<210> SEQ ID NO 2
<211> LENGTH: 20
<212> TYPE: DNA
<213> ORGANISM: Artificial Sequence
<220> FEATURE:
<223> OTHER INFORMATION: Bcl2 reverse primer

<400> SEQUENCE: 2
gagacagcca ggagaaatca                                              20

<210> SEQ ID NO 3
<211> LENGTH: 22
<212> TYPE: DNA
<213> ORGANISM: Artificial Sequence
<220> FEATURE:
<223> OTHER INFORMATION: Xiap forward primer

<400> SEQUENCE: 3
ctgaaaaaac accaccgcta ac                                           22

<210> SEQ ID NO 4
<211> LENGTH: 26
<212> TYPE: DNA
<213> ORGANISM: Artificial Sequence
<220> FEATURE:
<223> OTHER INFORMATION: Xiap reverse primer

<400> SEQUENCE: 4
ctaaatccca ttcgtatagc ttcttg                                       26

<210> SEQ ID NO 5
<211> LENGTH: 20
<212> TYPE: DNA
<213> ORGANISM: Artificial Sequence
<220> FEATURE:
<223> OTHER INFORMATION: Mdm2 forward primer

<400> SEQUENCE: 5
cggcctaaaa atggctgcat                                              20

<210> SEQ ID NO 6
<211> LENGTH: 22
<212> TYPE: DNA
<213> ORGANISM: Artificial Sequence
<220> FEATURE:
<223> OTHER INFORMATION: Mdm2 reverse primer

<400> SEQUENCE: 6
tttgcacacg tgaaacatga ca                                           22

<210> SEQ ID NO 7
<211> LENGTH: 22
<212> TYPE: DNA
<213> ORGANISM: Artificial Sequence
<220> FEATURE:
<223> OTHER INFORMATION: Hsp90aa  forward primer

<400> SEQUENCE: 7
ctccaattca tcggacgctc tg                                           22
```

```
<210> SEQ ID NO 8
<211> LENGTH: 22
<212> TYPE: DNA
<213> ORGANISM: Artificial Sequence
<220> FEATURE:
<223> OTHER INFORMATION: Hsp90aa reverse primer

<400> SEQUENCE: 8
tcaagtcggc cttggtcatt cc                                              22

<210> SEQ ID NO 9
<211> LENGTH: 20
<212> TYPE: DNA
<213> ORGANISM: Artificial Sequence
<220> FEATURE:
<223> OTHER INFORMATION: Gapdh forward primer

<400> SEQUENCE: 9
tgcctcctgc accaccaact                                                 20

<210> SEQ ID NO 10
<211> LENGTH: 19
<212> TYPE: DNA
<213> ORGANISM: Artificial Sequence
<220> FEATURE:
<223> OTHER INFORMATION: Gapdh reverse primer

<400> SEQUENCE: 10
cgcctgcttc accaccttc                                                  19
```

ANASTASIS BIOSENSOR

CROSS-REFERENCE TO RELATED APPLICATIONS

This application claims priority to U.S. patent application Ser. No. 14/383,156, filed Sep. 5, 2014, which is a 35 U.S.C. § 371 U.S. national entry of International Application PCT/US2013/029594, having an international filing date of Mar. 7, 2013, which claims the benefit of U.S. Provisional Application No. 61/607,799, filed Mar. 7, 2012, the content of each of the aforementioned applications is herein incorporated by reference in their entirety.

STATEMENT OF GOVERNMENTAL INTEREST

This invention was made with government support under grant no. GM046425 awarded by the National Institutes of Health. The government has certain rights in the invention.

FIELD OF THE INVENTION

The present invention relates to the field of anastasis, i.e., the process of reversal of apoptosis. More specifically, the present invention provides methods and compositions useful for studying anastasis.

INCORPORATION-BY-REFERENCE OF MATERIAL SUBMITTED ELECTRONICALLY

This application contains a sequence listing. It has been submitted electronically via EFS-Web as an ASCII text file entitled "P11872-02_Sequence_Listing.txt." The sequence listing is 2,134 bytes in size, and was created on Mar. 7, 2013. It is hereby incorporated by reference in its entirety.

BACKGROUND OF THE INVENTION

The discovery of programmed cell death, known as apoptosis (Greek for "falling to death"), was one of the most exciting and important breakthroughs in biology during the 20th century. Apoptosis is critical for normal embryonic development and adult homeostasis. Impaired apoptosis causes cancer whereas excess apoptosis contributes to major diseases including heart failure and neurodegeneration. Apoptosis is thought to be irreversible after mitochondrial fragmentation and effector caspase activation because, apart from mitochondrial dysfunction, which alone can lead to cell death, initiation of explosive caspase activation causes massive destruction of structural and functional cellular components including the genome. Activated caspases stimulate additional caspases, resulting in the morphological manifestations of apoptosis such as nuclear condensation, cell shrinkage, and membrane blebbing. After mitochondrial release of death effectors including cytochrome c, it is assumed that caspase activation and apoptosis inevitably follow.

An unexpected reversibility of late-stage apoptosis was recently discovered, which is called anastasis (Greek for "rising to life"). The vast majority of primary mouse liver and NIH3T3 human fibroblasts can reverse apoptosis and survive, even after the cells pass through critical checkpoints generally thought to be the point of no return including mitochondrial fragmentation and caspase-3 activation. Simply removing the apoptotic inducers by washing is sufficient to promote reversal of the process, indicating for the first time that anastasis is a mechanism that allows normal cells to arrest at the execution stage and ultimately recover. Notably, the cells that reverse apoptosis acquire genetic alterations and exhibit an increased frequency of colony formation in soft agar and anchorage independent growth. While oncogenic transformation is a negative consequence, the present inventors propose that there may also be multiple beneficial effects of this process. For example, anastasis may have evolved to salvage cells that are difficult to replace, such as mature neurons in the aging brain or adult heart cells. An organism may be better off preserving such cells, even if they are damaged, rather than allowing them to die.

Accordingly, new and innovative approaches are needed to study this newly discovered and fundamental cellular process. Elucidation of the mechanisms governing and executing anastasis could transform scientific understanding and lead to entirely new strategies for the prevention and treatment of degenerative diseases, ischemic diseases, and cancer.

SUMMARY OF THE INVENTION

The present invention is based, at least in part, on the discovery that normal cells can reverse apoptosis late in the process even after caspase-3 activation and DNA damage have occurred. In studying the reversal of apoptosis, termed "anastasis", the present inventors have designed and developed an in vivo biosensor. In one embodiment, the biosensor is useful for studying anastasis in Drosophila. The biosensor results in permanent GFP expression in any cell that survives after caspase activation. For example, in female flies subjected to protein starvation, germ cells undergo apoptosis and expression of GFP was observed when flies are starved and re-fed, indicating that at least some cells reverse apoptosis and survive in vivo. Accordingly, in certain embodiments, the biosensors of the present invention can be used to elucidate which cells can undergo anastasis in living animals after they are transiently subjected to stresses that are known to induce apoptosis. The retina is a unique tissue because it is accessible to long term observation in living animals. Therefore, in particular embodiments, the biosensors can be used to study the reversibility of apoptosis in photoreceptor cells of the retina. It will be of great importance to elucidate the molecular mechanisms by which cells reverse apoptosis and survive. Thus, the present invention can further be utilized to identify specific regulators of anastasis using a novel RNA interference screen. In further embodiments, the anastasis biosensor approach can be used in transgenic animals, e.g., mice, to determine whether primary cells isolated from such mice, particularly neurons and heart muscle cells, undergo anastasis.

Accordingly, in one embodiment, the present invention provides an in vivo biosensor comprising (a) a transcription factor complex comprising the Gal4 transcription factor linked to an enzyme cleavable linker, wherein the transcription factor complex is tethered to the plasma membrane via a transmembrane domain; and (b) a reporter system comprising (1) a first nucleic acid encoding flippase operably linked to the upstream activating sequence that binds Gal4; and (2) a second nucleic acid comprising an FRT-flanked stop codon cassette separating a constitutive promoter and a fluorescent protein open reading frame. In another embodiment, the enzyme cleavable linker is cleaved by an enzyme specifically expressed during apoptosis. In a specific embodiment, the enzyme is caspase. In a more specific embodiment, the fluorescent protein comprises green fluorescent protein, red fluorescent protein, or yellow fluorescent protein. In another method of the present invention, a transgenic mammal comprises a biosensor described herein. The transcription factor complexes of the present invention can further comprise a nuclear translocation signal.

In certain embodiments, the present invention provides a biosensor for studying anastasis comprising (a) a caspase-activatable transcription factor complex comprising Gal4 transcription factor linked to (1) a caspase-cleavable linker and (2) a transmembrane domain; and (b) a reporter system comprising a (1) first nucleic acid encoding flippase operably linked to the upstream activating sequence that binds Gal4; (2) a second nucleic acid comprising an FRT-flanked stop cassette separating a constitutive promoter and a fluorescent protein open reading frame. In a specific embodiment, the caspase-cleavable linker comprises the amino acid sequence DEVD. In another specific embodiment, the constitutive promoter is the ubiquitin promoter.

A biosensor of the present invention may comprise (a) a caspase-activatable transcription factor complex comprising Gal4 transcription factor linked to (1) a caspase-cleavable linker and (2) a transmembrane domain; and (b) the G-TRACE reporter system. A biosensor can also comprise (a) a caspase-activatable recombinase complex comprising Cre recombinase protein linked to (1) a caspase-cleavable linker and (2) a transmembrane domain; and (b) a nucleic acid comprising a LoxP-flanked stop cassette separating a constitutive promoter and a fluorescent protein open reading frame.

In yet another embodiment, the present invention provides a biosensor system comprising (a) a site-specific recombinase tethered to the plasma membrane of a test cell, wherein the recombinase is linked to a transmembrane domain via an enzyme cleavable linker; and (b) a nucleic acid encoding a reporter gene operably linked to a promoter, wherein the recognition target sequence of the recombinase flanks a stop codon cassette located between the reporter gene and the promoter. In a specific embodiment, the site-specific recombinase is flippase and the recognition target sequence is FRT. In another embodiment, the reporter gene encodes a fluorescent protein. In a further embodiment, the promoter is a constitutive promoter. In yet another embodiment, the enzyme is caspase.

Any transcription factor/recognition sequence of the transcription factor can be used in the present invention. In particular embodiments, an in vivo biosensor comprises (a) a transcription factor complex comprising a transcription factor linked to an enzyme cleavable linker, wherein the transcription factor complex is tethered to the plasma membrane via a transmembrane domain; and (b) a reporter system comprising (1) a first nucleic acid encoding a site specific recombinase operably linked to the site specific sequence for the transcription factor; and (2) a second nucleic acid comprising a stop codon cassette flanked by site specific recombination sequences, wherein the stop codon cassette and flanking sequences separate a constitutive promoter and a fluorescent protein open reading frame. In one embodiment, the enzyme cleavable linker is cleaved by an enzyme specifically expressed during apoptosis. In a more specific embodiment, the enzyme is caspase. In another embodiment, the fluorescent protein comprises green fluorescent protein, red fluorescent protein, or yellow fluorescent protein.

In yet a further embodiment, a biosensor comprises a nucleic acid comprising a stop codon cassette flanked by site specific recombinase recombination sequences, wherein the stop codon cassette and flanking sequences separate a constitutive promoter and a fluorescent protein open reading frame. In another more specific embodiment, the recombinase is a recombinase expressed only during apoptosis.

In another embodiment, the site specific recombinase, e.g., Cre, is split, for example, N-terminal Cre and the C-terminal Cre. In one embodiment, one part of the split Cre can be tethered to the cell membrane using a caspase cleavable linker. The other part of Cre can be expressed, for example, in mitochondria.

BRIEF DESCRIPTION OF THE FIGURES

FIG. 3A is a schematic diagram of the caspase biosensor, NES-DEVD-YFP-NLS. NES: nucleus exclusion signal; DEVD: caspase cleavable sequence; YFP: Yellow fluorescent protein; NLS: nucleus localization signal. FIG. 3B shows real-time living cell microscopy of HeLa cell before (untreated), during (Treated) and after (Washed) exposure to 4.5% ethanol. Merged images: caspase biosensor (GFP) and nuclei (blue) were visualized by fluorescence, and cell morphology by DIC microscopy. Time is shown in hr:min.

FIG. 4A shows the percentage of the untreated and the washed liver and NIH3T3 cells displaying abnormality in chromosomal configuration. FIG. 4B shows the number of foci of the untreated and the reversed NIH3T3 cell cultures at the third week of culture. FIG. 4C shows the number of colonies formed in soft agar of the untreated and the reversed NIH3T3 cells after 5 weeks of culture. *P<0.05; n=3. Error bars denote s.d.

FIG. 5A: in healthy cells, Gal4 protein is tethered to the plasma membrane via a caspase-cleavable linker peptide and a transmembrane domain.

FIG. 5B: upon caspase activation in apoptosis, the peptide is cleaved and Gal4 is released and translocates to nucleus. This activates a Gal-4 dependent genetic recombination event by Gal-4 driven expression of FLP recombinase (G-TRACE) (FIG. 5C), which then excises the FRT-flanked stop cassette separating the Ubi promotor and green fluorescent protein (GFP) open reading frame (FIG. 5D), resulting in permanent expression of GFP in the cell as well as its progeny (FIG. 5E).

FIG. 7A: in a healthy cell, Cre protein is tethered to the plasma membrane via a caspase-cleavable linker peptide and a transmembrane domain. FIG. 7B: upon caspase activation, the peptide is cleaved and Cre is released and translocates to the nucleus. This activates Cre driven a genetic recombination event (Cre-Lox), which then excises the stop cassette separating the promotor and green fluorescent protein (GFP) open reading frame (FIG. 7C), resulting in permanent expression of GFP in the cell as well as its progeny (FIG. 7D).

(FIG. 10A) Time-lapse live-cell fluorescence microscopy of a primary liver cell before, during, and after exposure to ethanol. The same cell before ethanol induction (Untreated, i), induced with 4.5% ethanol in culture medium for 2.5 h (Treated, ii and iii), and then washed and further cultured with fresh medium (Washed, iv-vi). Merged images, mitochondria (red) and nuclei (blue) were visualized by fluorescence and cell morphology by DIC. Time presented as h:min. Scale bar, 10 μm. (FIG. 10B) Monochrome images of mitochondria from A. Mitochondrial fragmentation is indicated by red arrows. (FIG. 10C) Fluorescence and DIC microscopy of healthy liver and NIH 3T3 cells (Untreated), cells that were exposed to apoptotic inducers (liver cells, 4.5% ethanol for 5 h; NIH 3T3 cells, 10% DMSO for 20 h) (Treated), and treated cells that were washed to remove apoptotic inducers and further cultured for 24 h (Washed). Merged images, mitochondria (red), nuclei (blue), and Quantum Dots (Qdots) taken up by endocytosis (green) were visualized by fluorescence and cell morphology by DIC. Scale bar, 10 μm. (FIG. 10D) Quantification of the apoptotic response and its reversal. Morphological signs of apoptosis included nuclear condensation, mitochondrial fragmentation, and cell shrinkage. Uptake of Quantum Dots by endocytosis is characteristic of healthy cells, whereas the other features are characteristic of apoptotic cells. Apoptosis was induced in liver cells with 4.5% ethanol for 5 h and in NIH 3T3 cells with 10% DMSO for 20 h (Treated). Treated cells were then washed and further cultured for 24 h in standard conditions. *$p<0.01$; n=3 independent experiments. Error bars denote SD. (FIG. 10E) Western blot analysis of the total cell lysate of untreated, treated, and washed liver and NIH 3T3 cells for the protein level of caspase-3 (Casp-3). c, cleaved form. (FIG. 10F) Schematic diagram of the caspase biosensor NES-DEVD-YFP-NLS. (FIG. 10G) Real-time live-cell microscopy of HeLa cells expressing the caspase biosensor before (Untreated, i), during (Treated, ii and iii), and after (Washed, iv-vi) exposure to 4.3% ethanol. Merged images, caspase biosensor (YFP, green) and nuclei (blue) were visualized by confocal microscopy and cell morphology by DIC. Corresponding monochromatic YFP image is shown in each panel. Time presented as h:min. Scale bar, 10 μm. (FIG. 10H) Quantification of the caspase biosensor response in HeLa cells. Treated cells were exposed to 4.3% ethanol for 5 h. After washing, cells were cultured for 2 h in standard conditions. *$p<0.01$; n=3 independent experiments. Error bars denote SD.

(FIG. 11A) Schematic diagram of approach using annexin V-FITC to track cells that reverse apoptosis. (FIG. 11B) Confocal and DIC microscopy of rat primary heart cells that were exposed to 4.5% ethanol for 5 h (Treated) or not (Untreated). Treated cells were then washed to remove apoptotic inducers and further cultured for 2 h (Washed). Merged images, mitochondria (red), nuclei (blue), and annexin V-FITC (annexin V)-labeled exposed phosphatidylserine (PS) (green) were visualized by fluorescence, and cell morphology was by DIC. Scale bar, 10 μm. (FIG. 11C) Quantification of the apoptotic response and its reversal on primary rat heart cells and Mpf brain cells. Percentage of cells showing morphological signs of apoptosis including mitochondrial fragmentation, nuclear condensation, cell shrinkage, and cell surface phosphatidylserine labeled with annexin V-FITC (Annexin V) for control cells (Untreated), cells treated with apoptotic inducer (heart cells with 4.5% ethanol for 5 h, brain cells with 2 μM jasplakinolide for 50 h) (Treated), and treated cells that were washed and further cultured with fresh medium (heart cells for 2 h, brain cells for 3 h) in standard conditions (Washed). *$p<0.01$; n=3 independent experiments. Error bars denote SD. (FIG. 11D) Fluorescence of healthy, untreated macrophages, those that were exposed to 1 μM cucurbitacin I (CuI) for 24 h (Treated), and treated cells that were washed to remove apoptotic inducers and further cultured for 24 h (Washed). Merged images, mitochondria (red) and nuclei (blue). Scale bar, 30 μm. (FIG. 11E) Percentage of the untreated, treated, and washed macrophages that displayed mitochondrial fragmentation, nuclear condensation, and cell shrinkage. *$p<0.01$; n=3 independent experiments. Error bars denote SD.

FIG. 12A-12J: Damage of DNA in dying cells before reversal of apoptosis. (FIG. 12A) Fluorescence micrographs showing the subcellular localization of AIF (green), EndoG (red), and nuclei (blue) in primary liver cells that were untreated (Untreated) or treated with 4.5% ethanol for 5 h (Treated) and treated cells that were then cultured for 24 h in fresh medium after removal of the ethanol (Washed) from cells. Quantification of the corresponding fluorescence signals of AIF, EndoG, and nucleus along the dotted line as indicated in their respective images. Scale bar, 10 μm. (FIG. 12B) Percentage of liver and NIH 3T3 cells that displayed nuclear accumulation of AIF and EndoG. Treated liver cells were exposed to 4.5% ethanol for 5 h. NIH 3T3 cells were treated with 10% DMSO for 20 h. Treated cells that were then washed to remove apoptotic inducers were further cultured for 24 h (Washed). *$p<0.01$; n=3 independent experiments. Error bars denote SD. (FIG. 12C, FIG. 12D) Western blot analysis of total cell lysates of untreated, treated, and washed liver and NIH 3T3 cells were probed for (C) PARP and (D) ICAD. c, cleaved form. (FIG. 12E) Fluorescence microscopy for the SYBR-stained DNA of untreated, treated, and washed liver cells subjected to the comet assay for DNA damage. Cells embedded in agarose were subjected to electrophoresis. Broken DNA forms comet tails such as the one indicated by an arrow. Intact DNA remains within the nuclear envelop. (FIG. 12F) Percentage of untreated, treated, and washed liver and NIH 3T3 cells that displayed a comet tail. **$p<0.01$; n=3 independent experiments. Error bars denote SD. (FIG. 12G) Fluorescence microscopy on nuclear morphology of untreated as well as treated and washed primary liver cells 16 h after removal of apoptotic inducer. Cytokinesis was blocked with cytochalasin B (Cyto B). Arrows indicate micronuclei in the washed cells. Scale bar, 10 µm. (FIG. 12H) Percentage of untreated, as well as treated and then washed, liver, NIH 3T3, and HeLa cells that displayed micronuclei. Apoptotic inductions for the liver and NIH 3T3 cells were as described in (FIG. 12B) and for HeLa as in (FIG. 12J). *p<0.05; **p<0.01; n=3 independent experiments. Error bars denote SD. (FIG. 12I) Proposed model for the formation of micronuclei in cells that divide after reversal of apoptosis, likely as a result of unrepaired DNA damage. (FIG. 12J) Time-lapse live-cell fluorescence microscopy of HeLa cells before, during, and after exposure to ethanol. The same cell before ethanol induction (Untreated, i), induced with 4.3% ethanol in culture medium for 5 h (Treated, ii), and then washed and further cultured with fresh medium (Washed, iii-x). Monochromatic images of nuclei stained with Hoechst 33342. Arrows indicate some of the micronuclei. Time presented as h:min. Scale bar, 30 µm. Cytochalasin B was not present in this experiment.

FIG. 13A-13H: Genetic alterations and transformation after reversal of apoptosis. (FIG. 13A) Inverted DAPI-banding image of metaphase spreads of untreated liver cells (Untreated) compared with cells that were treated with 4.5% ethanol for 5 h, washed, and then cultured for 3 d after removal of apoptotic inducer (Washed). The number of metaphase chromosomes is indicated on the corresponding images. An abnormal chromosomal configuration is indicated by an arrow. (FIG. 13B) Percentage of untreated and washed liver cells (3 d after 5-h exposure to 4.5% ethanol) and NIH 3T3 cells (3 d after 20-h exposure to 10% DMSO) displaying the indicated number of chromosomes in metaphase spreads. ns, p>0.05; *p<0.05; **p<0.01; n=3 independent experiments. Error bars denote SD. (FIG. 13C) Representative inverted DAPI-banding images of the configuration of metaphase chromosomes of untreated (Untreated) as well as treated and washed (Washed) liver cells. Configurations indicated by arrows: triradial (TR, red); quadriradial (QR, blue); complex figures (CF, green); deletion (DE, black). (FIG. 13D) Percentage of the untreated and the washed liver and NIH 3T3 cells displaying at least one abnormality in chromosomal configuration. *p<0.05; n=3 independent experiments. Error bars denote SD. (FIG. 13E) Image of untreated NIH 3T3 cells and the foci from the cells after being treated and washed (Washed) after 3 wk of culture. Scale bars: 50 µm. (FIG. 13F) Number of foci in untreated as well as treated and washed NIH 3T3 cells after 3 wk of culture. *p<0.05; n=3 independent experiments. Error bars denote SD. (FIG. 13G) Image of crystal violet-stained colonies in soft agar in untreated as well as treated and washed NIH 3T3 cells from the foci after 5 wk of culture. Inset, enlarged image of a colony. Scale bars, 400 µm (white), 2 mm (black). (FIG. 13H) Number of colonies formed in soft agar in untreated as well as treated and washed NIH 3T3 cells after 5 wk of culture. *p<0.05; n=3 independent experiments. Error bars denote SD.

(FIG. 14A) RNA blot for detecting new RNA synthesis in untreated vs. treated and washed (Washed) liver cells 1 h after a 5-h exposure to 4.5% ethanol and with and without transient exposure (1 h, 1 µg/ml) to actinomycin D (AMD). No s4U served as negative control for the probe binding to RNA. (FIG. 14B) Western blot analysis of the cleavage of caspase-3 (Casp-3) on the total lysate of untreated, treated (5-h exposure to 4.5% ethanol for liver cells, 20-h exposure to 10% DMSO for NIH 3T3 cells), and washed liver cells and NIH 3T3 cells with and without transient exposure to actinomycin D (AMD) immediately after removal of apoptotic stimuli. The AMD-exposed cells were cultured in fresh medium for 23 h and then subjected to the analysis. c, cleaved form. (FIG. 14C) Percentage of untreated as well as treated and washed liver cells and NIH 3T3 cells with and without transient AMD exposure that displayed plasma membrane permeability in trypan blue exclusion assay. The AMD exposed-cells were cultured in fresh medium for 23 h and then subjected to the assay. ns, p>0.05; *p<0.05; n=3 independent experiments. Error bars denote SD. (FIG. 14D) A time-course microarray study in liver cells, log 2-fold change of gene expression comparison between ethanol-induced apoptotic cells (RO), untreated cells (Ctrl), and induced cells that were then washed and further cultured in fresh medium for 3 (R3), 6 (R6), 24 (R24), and 48 h (R48). The log 2 signal values from three biological replicates were averaged (geometric mean) for each time point. (FIG. 14E) Percentage of untreated and washed liver cells with and without 24-h exposure of inhibitors of BCL-2 (ABT 263, 1 µM), XIAP (Embelin, 20 µM), MDM2 (Nutlin-3, 10 µM), and HSP90 (17-allylaminogeldanamycin, 0.5 µM) that displayed full plasma membrane permeability in trypan blue exclusion assay. The corresponding cells were exposed to the inhibitors after apoptotic stimuli had been removed from the treated cells and then further cultured for 24 h. ns, p>0.05; *P<0.05; n=3 independent experiments. Error bars denote SD. (FIG. 14F) Proposed model for reversal of apoptosis. Expression of multiple prosurvival factors and new transcripts during reversal of apoptosis promotes cell survival by suppressing the activated apoptotic pathways and repairing the cells.

DETAILED DESCRIPTION OF THE INVENTION

Figures 1A, 1B, 1C, 1D, 1E, 1F:
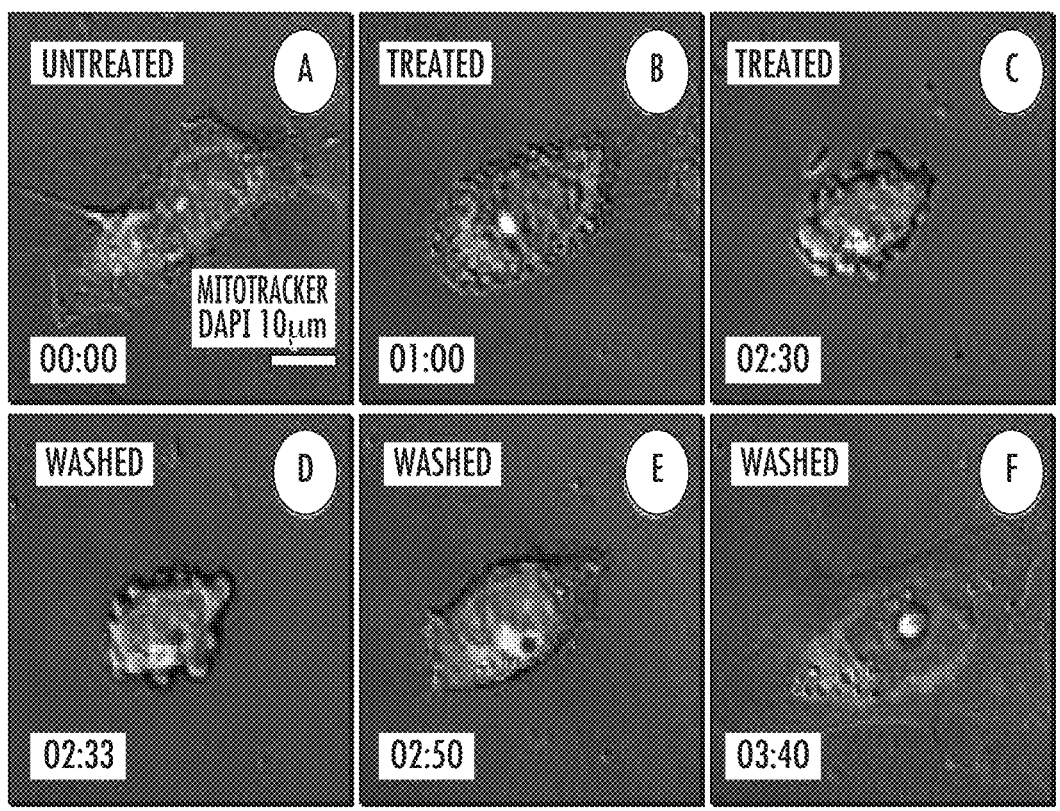
FIG. 1A-1F shows the reversibility of apoptosis in primary mouse liver cells. Real-time living cell microscopy of a primary liver cell before (untreated) (FIG. 1A), during (treated) (FIG. 1B-1C) and after (washed) (FIG. 1D-1F) exposure to 4.5% ethanol. Merged images: mitochondria (red) and nuclei (blue) were visualized by fluorescence, and cell morphology by DIC microscopy. Time is shown in hr:min.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided. The definitions are not meant to be limiting in nature and serve to provide a clearer understanding of certain aspects of the present invention.

The present inventors have shown that cells that initiate apoptosis under stressful conditions and then reverse that process, survive and proliferate, although a small fraction of surviving cells harbor lasting DNA damage. The present inventors propose that reversal of apoptosis can salvage precious cells that are difficult to replace but can also lead to pathophysiological consequences such as oncogenic transformation. In germ cells, such stress-induced mutagenesis could enhance genetic and phenotypic diversity in the progeny of an animal population, precisely when organisms find themselves maladapted to their environment. Therefore one of the potentially paradigm shifting implications of anastasis is that it could in principle accelerate evolution by natural selection. Studying the mechanisms regulating anastasis using the biosensors of the present invention has the potential not only to reveal new strategies and targets for the treatment of apoptosis-related diseases, but also to enhance our understanding of evolution.

As used herein, the term "polynucleotide" or "nucleic acid" refers to a polymeric form of nucleotides of any length, either ribonucleotides and/or deoxyribonucleotides. These terms include a single-, double- or triple-stranded DNA, genomic DNA, cDNA, RNA, DNA-RNA hybrid, or a polymer comprising purine and pyrimidine bases, or other natural, chemically, biochemically modified, non-natural or derivatized nucleotide bases. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidates and thus can be an oligodeoxynucleoside phosphoramidate (P—NH$_2$) or a mixed phosphoramidate-phosphodiester oligomer. In addition, a double-stranded polynucleotide can be obtained from the single stranded polynucleotide product of chemical synthesis either by synthesizing the complementary strand and annealing the strands under appropriate conditions, or by synthesizing the complementary strand de novo using a DNA polymerase with an appropriate primer.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The term "promoter" refers to the DNA region, usually upstream of the coding sequence of a gene or operon, which binds RNA polymerase and directs the enzyme to the correct transcriptional start site.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors," which comprise the attributes of more than one type of vector A "site-specific recombination event" refers to an event catalyzed by a system generally consisting of three elements: a pair of DNA sequences (the site-specific recombination sequences or sites) and a specific enzyme (the site-specific recombinase). The site-specific recombinase catalyzes a recombination reaction only between two site-specific recombination sequences depending on the orientation of the site-specific recombination sequences. Sequences intervening between two site-specific recombination sites will be inverted in the presence of the site-specific recombinase when the site-specific recombination sequences are oriented in opposite directions relative to one another (i.e., inverted repeats). If the site-specific recombination sequences are oriented in the same direction relative to one another (i.e., direct repeats), then any intervening sequences will be deleted upon interaction with the site-specific recombinase. Thus, if the site-specific recombination sequences are present as direct repeats at both ends of vector backbone sequences integrated into a eukaryotic genome, such integration of said sequences can subsequently be removed by interaction of the site-specific recombination sequences with the corresponding site specific recombinase.

A number of different site specific recombinase systems can be used including, but not limited to, the Cre/lox system of bacteriophage P1, the FLP/FRT system of yeast, the Gin recombinase of phage Mu, the Pin recombinase of *E. coli*, the PinB, PinD and PinF from *Shigella*, and the R/RS system of *Zygosaccharomyces rouxii*. Recombinases generally are integrases, resolvases or flippases. Also dual-specific recombinases can be used in conjunction with direct or indirect repeats of two different site-specific recombination sites corresponding to the dual-specific recombinase (WO99/25840). In certain embodiments, site-specific recombinase systems are the bacteriophage P1 Cre/lox and the yeast FLP/FRT and the *Z. rouxii* R/RS systems. In these systems a recombinase (Cre, FLP or R, respectively) interact specifically with its respective site-specific recombination sequence (lox, FRT or RS respectively) to invert or excise the intervening sequences. The site-specific recombination sequences for each of these two systems are relatively short (34 bp for lox and 47 bp for FRT).

Discussion

Apoptosis is critical in multicellular organisms (Kerr et al., 1972; Jacobson et al., 1997; Fuchs and Steller, 2011). It is widely accepted that there are both proapoptotic and antiapoptotic signals in cells, and the balance between the two determines whether a cell lives or dies. Although the precise point of no return may vary in different cell types and conditions (Kroemer et al., 2009), it has generally been assumed that apoptosis is irreversible after caspase activation and DNA damage (Riedl and Shi, 2004; Taylor et al., 2008; Chipuk et al., 2010). Strikingly, the time-lapse live imaging and biochemical studies reported here reveal that apoptotic cells can survive and reverse the process of dying even after they have reached an advanced stage of apoptosis, including caspase-3 activation and even DNA damage. This phenomenon was not limited to one cell type or apoptotic inducer but rather was observed for different types of cells and inducers. We propose to name this process anastasis, 1 which is a Greek word that means "rising to life" and thus represents an apt contrast to the word apoptosis (Kerr et al., 1972), which is a Greek word meaning "falling to death."

Although it was surprising to observe cells recovering normal cell morphology after reaching such an advanced stage of apoptosis, in a few other biological contexts it is known that substantial caspase activation does not obligatorily lead to cell death. One example is sperm maturation in

*Drosophila melanogaster* (Arama et al., 2003). Late in sperm development, most of the spermatocyte cytoplasmic contents are destroyed in a process that requires apoptosome components and caspase activity. In this case, apoptosis proceeds part way and then stops but does not actually reverse. Presumably sperm DNA is protected from damage, although this has not been examined directly.

In another example, we previously reported reversible apoptosis in human cancer cells after various inductions (Tang et al., 2009). Here we show that removal of apoptotic inducers was sufficient to promote anastasis in primary cells, indicating that it is an endogenous mechanism and suggesting that it is a normal physiological process rather than a function restricted to abnormal cells. The present study also suggests that anastasis may be a general phenomenon in mammalian cells.

Of interest, chromosomal abnormalities and oncogenic transformation of primary liver cells and NIH 3T3 fibroblasts occurred after reversal of apoptosis. These observations suggest that anastasis could represent a previously unrecognized cause of genetic alterations. It also represents a form of stress-induced mutagenesis, possibly analogous to that described in prokaryotic and eukaryotic organisms (McClintock, 1984; Capy et al., 2000; Rosenberg, 2001; Jiang et al., 2003). In bacteria and plants, stress-induced mutagenesis has been proposed to accelerate evolution by natural selection by increasing the mutation frequency precisely when organisms find themselves maladapted to their environments.

The observation that anastasis can occur in normal cells has multiple intriguing implications. For example, anastasis could represent one mechanism underlying the observation that repeated injury increases the risk of cancer in a variety of tissues (Boffetta and Hashibe, 2006). Alcohol abusers are more prone to liver cancer (McKillop and Schrum, 2005), and massive apoptosis has been observed in mouse liver after exposure to ethanol (Goldin et al., 1993). Here we show that transient exposure of primary liver cells to high concentrations of ethanol caused them to initiate and then reverse apoptosis, increasing the frequency of oncogenic transformation. Therefore reversal of apoptosis could be a mechanism that allows cells to survive a transient crisis but then results in genomic rearrangements similar to those recently reported in cancer genome sequencing studies (Liu et al., 2011; Stephens et al., 2011).

Reversal of apoptosis could also be a mechanism by which cancer cells initially survive chemotherapy and radiation treatments and later evolve resistance. As we show here, cells that reverse apoptosis may acquire new mutations from the dying process, in addition to the direct mutagenic effects of radiation and chemotherapy drugs (Ross, 1999; Johnstone et al., 2002; Fu et al., 2012). Therefore cancer cells that undergo reversal of apoptosis after anticancer treatment could acquire new mutations and thus transform into more aggressive and metastatic cancers. Acquisition of mutations in normal cells as a consequence of reversal of apoptosis might also cause new tumors after cycles of anticancer therapy.

In addition to its pathophysiological implications such as oncogenesis, a possible beneficial effect of anastasis could be to preserve injured cells that are difficult to replace, such as mature neurons and heart cells. Neuronal cell death occurs, for example, in the retinas of flies, rabbits, and rats after exposure to excess light (McKechnie and Foulds, 1980; Milligan et al., 1997; Gordon et al., 2002). Of interest, the features of apoptosis vanish quickly in the corresponding tissues when the environment improves (McKechnie and Foulds, 1980; Milligan et al., 1997; Gordon et al., 2002). During heart failure, significant numbers of cells release cytochrome c and activate caspase-3 but manage to maintain normal nuclear morphology (Narula et al., 1999; Reed and Paternostro, 1999), suggesting arrest of the apoptotic process in heart cells (Narula et al., 2006). The results shown here suggest that heart cells can even reverse the apoptotic process.

Environmental stresses also trigger apoptosis in germ cells in mammals and other organisms (Aitken et al., 2011). For example, in *Drosophila melanogaster* and *Caenorhabditis elegans*, germ cells undergo apoptosis in response to starvation (Drummond-Barbosa and Spradling, 2001; Salinas et al., 2006). In this setting, reversal of apoptosis, if it occurs, could in principle promote genetic diversity and thereby accelerate evolution by natural selection, specifically in stressful environmental conditions. Further investigations of this newly discovered process will be necessary to test these hypotheses, with significant implications for our understanding of development, homeostasis, diseases, and evolution.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Cell Culture.

Primary liver cells were isolated from BALB/c mice by collagenase B according to the manufacturer's instructions (Worthington Biochemical, Lakewood, N.J.) and cultured as described (Zurlo and Arterburn, 1996). Primary cultures of heart cells were dissociated from ventricles of 1- or 2-d-old neonatal Sprague Dawley rats (Harlan, Indianapolis, Ind.) by enzymatic digestion of 0.1% trypsin overnight (US Biochemicals, Cleveland, Ohio) and then 0.1% collagenase (Worthington Biochemical) for dissociation as previously described (Iravanian et al., 2003). Peritoneal macrophages were isolated from BALB/c mice as previously described (Hu et al., 2009). NIH 3T3 cells, human cervical cancer HeLa cells, and Mpf brain cells (CRL 1656) were purchased from the American Type Culture Collection (Manassas, Va.). The cells were cultured in DMEM/F-12 (DMEM:nutrient mixture F-12) supplemented with 10% fetal bovine serum, 100 U/ml penicillin, and 100 µg/ml streptomycin (Life Technologies, Carlsbad, Calif.) at 37° C. under an atmosphere of 5% $CO_2$/95% air. Cells were seeded onto tissue culture plates for 2 d with 70% confluence before being subjected to each experiment. The medium was changed every 24-36 h.

Apoptotic Inductions.

Unless specifically mentioned, apoptosis in the primary mouse liver cells and primary rat heart cells was induced by 5-h exposure to 4.5% ethanol (Scharlau, Barcelona, Spain), HeLa cells by 5-h exposure to 4.3% ethanol, and NIH 3T3 cells by 20-h exposure in 10% DMSO (Sigma-Aldrich, St. Louis, Mo.) in culture medium (vol/vol). Mpf cells were induced by 50-h incubation in 2 µM jasplakinolide (Invitrogen, Carlsbad, Calif.) and primary mouse macrophages by 24-h incubation in 1 µM cucurbitacin I (ChromaDex, Irvine, Calif.) in culture medium. These conditions were chosen because they represented the lowest concentration of inducer that caused >90% of cells to undergo apoptosis. For removal of apoptotic inducers, cells were washed three times with culture medium and then cultured for the period of time indicated in the individual experiments.

Immunocytochemistry and Fluorescence and Confocal Microscopy.

Mitochondria and nuclei were stained in living cells with 50 nM Mitotracker Red CMXRos and 250 ng/ml Hoechst 33342 (Invitrogen), respectively, for 20 min in culture medium. Cells with active endocytosis were labeled by green fluorescence-emitting Quantum Dots from Qtracker 525 Cell Labeling Kit (Invitrogen) as described (Jaiswal et al., 2003). ApoAlert pCaspase3-Sensor Vector (BD Clontech, San Jose, Calif.) was transfected to HeLa cells using X-tremeGENE 9 DNA Transfection Reagent (Roche, Indianapolis, Ind.). Cell surface membrane phosphatidylserine (PS) was detected by using Annexin V Apoptosis Detection Kit according to manufacturer's instructions (BioVision, Milpitas, Calif.). The cells were fixed with 3.7% (wt/vol) paraformaldehyde in phosphate-buffer saline (PBS) solution for 20 min at room temperature, and incubated with 0.1% Triton X-100 (vol/vol) (Sigma-Aldrich) for 10 min before immunostaining. Endogenous AIF and EndoG were stained with anti-AIF and anti-EndoG primary antibodies (Santa Cruz Biotechnology, Santa Cruz, Calif.) and conjugated with green fluorescent Alexa Fluor 488 and red fluorescent Alexa 594 anti-rabbit immunoglobulin G secondary antibodies with Zenon Tricolor Labeling kit (Invitrogen), respectively. Cell images were captured with a monochromatic CoolSNAP FX camera (Roper Scientific, Tucson, Ariz.) on an inverted fluorescence microscope Cell Observer Z1 using a 63×, numerical aperture (NA) 1.4 plan-Apochromat objective or LSM 710 on an upright microscope Axio Examiner using a 40×, NA 1.1W Corr LD C-Apochromat objective (Carl Zeiss, Jena, Germany). Images were analyzed by using AxioVision 4.2 software (Carl Zeiss).

Real-Time Live-Cell Microscopy.

Cells were cultured in CO2-independent medium (Invitrogen) on a glass-bottom culture dish (MatTek Corporation, Ashland, Mass.) or a thermo-cell culture FCS2 chamber (Bioptechs, Butler, Pa.), which was mounted onto the adapter in the stage of an inverted fluorescence microscope. Ethanol (4.5% for liver, 4.3% for HeLa cells [vol/vol]) in culture medium was introduced to the cells through perfusion tubes (Bioptechs), which were connected to the cell chamber. The ethanol was removed, and fresh medium was then introduced to the chamber through these tubes after apoptotic induction. Fluorescence signals of mitochondria and nuclei were visualized by fluorescence with excitation at 561 and 405 nm, respectively, and cell morphology by differential interference contrast (DIC) or phase contrast microscopy. Time-lapse images were captured by Cell Observer Z1 (Carl Zeiss) with a Monochromatic CoolSNAP FX Camera (Roper) or Evolve 128 EMCCD (Photometrics, Tucson, Ariz.) using a 63×, NA 1.4 Plan-Apochromat objective or a 40×, NA 0.95 Con Plan-Apochromat objective (Carl Zeiss), a BioStation IMQ time-lapse imaging system (CELL-S2) using a 40×, NA 0.8 Plan-Apochromat objective (Nikon, Melville, N.Y.), or a C2 Confocal on a TiE Invert microscope using a 60×, NA 1.4 Plan—Apochromat objective (Nikon). Images and heat map were analyzed by using AxioVision 4.2 software.

Western Blot Analysis.

Approximately 3 µg of protein from total cell lysate per lane was separated on a 12% SDS-PAGE gel and transferred onto a Hybond ECL membrane (Amersham Biosciences, Chalfont St Giles, United Kingdom). After blocking, the membrane was incubated overnight at 4° C. with primary antibody detecting targeted protein as stated in the text with 1:1000 dilution, followed by another hour of incubation with the corresponding horseradish peroxidase-conjugated secondary antibody (Bio-Rad, Hercules, Calif.) at room temperature with 1:5000 dilution. Primary antibodies used were as follows: anti-caspase-3, anti-PARP (Cell Signaling Technology, Danvers, Mass.), and anti-ICAD (BD PharMingen, BD Biosciences, Le Pont de Clax, France). The signal from the secondary antibody was detected with the ECL Western blotting detection system (Amersham-Pharmacia Biotech, GE Healthcare Bio-Sciences, Piscataway, N.J.).

Single-Cell Gel Electrophoresis (Comet) Assay.

Comet assay was performed by using the Trevigen Comet Assay kit (Trevigen, Gaithersburg, Md.) according to manufacturer's instructions. Alkaline electrophoresis of gelled slides was performed using Ready Sub-Cell GT Cells (Bio-Rad) on ice with 20 V and 200 mA for 30 min. The current was adjusted by the volume of the buffer in the gel tank. The DNA was visualized by SYBR Green staining (Trevigen), followed by fluorescence microscopy.

Cytokinesis-Block Micronucleus Assay.

Cells were grown on glass coverslips (Marienfeld, Lauda-Künigahofen, Germany) with 70% confluence in six-well cell culture plates (Nunc, Roskilde, Denmark) and were induced to apoptosis as described in the section Apoptotic Inductions. To study genomic damage in apoptotic cells that reversed apoptosis and proliferated, the apoptosis-induced cells were washed and cultured for 16 h in fresh medium that contained cytokinesis-blocking cytochalasin B (3 µg/ml; Sigma-Aldrich). Cells without apoptotic induction served as control. The cells were then fixed by incubating in methanol/acetic acid (5:1, vol/vol) twice for 15 min, followed by overnight fixation at 4° C. After washing three times with PBS, the fixed cells were stained for nuclei by incubation with 250 ng/ml Hoechst 33342 in PBS for 20 min at room temperature. Slides were then prepared as described for fluorescence microscopy and observed under a 63× objective to image micronucleus. The micronuclei in the cytokinesis-blocked cells were scored as described (Fenech, 2007). Only binucleated cells were scored, so as to include only cells that divided once after addition of cytochalasin B. The two main nuclei should have a clear boundary from each other, and micronuclei were counted only when clear boundary from the main nuclei was observed. The diameter of a micronucleus should lie between $1/16$ and $1/3$ that of the main nuclear diameter. Triplicates were performed, with >100 cells for each condition per set.

Karyotyping.

Metaphase chromosome spreads were prepared as described (MacLeod et al., 2007) with modifications. Briefly, cells were arrested at metaphase by adding colchicine (Sigma-Aldrich) at a final concentration of 1 μg/ml into growing culture for 6 h. The arrested cells were then collected by trypsinization with immediate neutralization with cell culture medium and then followed by 5 min of centrifugation at 400×g. After discarding the supernatant, we loosened the cell pellet by gentle flicking in residual medium. To swell the mitotic cells, we incubated the cell suspension in hypotonic buffer, potassium chloride (5.59 g/l in double-distilled water), and sodium citrate (9.0 g/l in double-distilled water) in 1:1 (vol/vol), for 8 and 15 min for NIH 3T3 and primary liver cells, respectively, at 37° C. The cells were then pelleted at 400× g for 5 min to remove the hypotonic buffer. The cells were then fixed by gently adding freshly prepared ice-cold fixative (methanol/acetic acid, 3:1, vol/vol) to the pellet while agitating the centrifuge tube for the whole time so as to prevent cell clumps formation and ensure thorough mixing. The fixative was changed once, and then the cells were fixed overnight at 4° C. Next, the cells were concentrated in fixative of a volume such that the suspension became slightly cloudy for optimal cell concentration. To spread the metaphase of the fixed cells onto slides, we dropped the cell suspension from height onto a chilly, precleaned SuperFrost Plus microscopic slide (Gerhard Menzel, Braunschweig, Germany) slightly sloped on a freezer block. Then the slides were breathed on to enhance spreading and were mounted with 4',6-diamidino-2-phenylindole (DAPI)/Antifade kit (MetaSystems, Altlussheim, Germany) after drying. The metaphase chromosomes of metaphase-arrested cells were identified and captured by an automated cytogenetic scanner workstation (MetaSystems) for analysis. Only metaphases of distinctly separated chromosomes and of chromosome spreading patterns from one nucleus were counted in order to avoid overlapped metaphases. Three replicates of >100 metaphases each were counted for the presence of radial configurations in each corresponding metaphase spread for chromosomal abnormality.

Transformation Assays.

For the focus formation assay, cells were seeded in 10-cm$^2$ culture dishes (Nunc) to reach 70% confluence. They were induced and washed as described. Then the culture medium was changed every 3 d. After 3 wk of culture, morphologically transformed foci whose diameter exceeded 0.5 mm were counted. The assay was performed three times. From each replicate, at least five transformed foci were isolated by picking with sterile pipette tip and were then cultured for soft agar assay. Anchorage-independent colony formation of NIH 3T3 cells undergoing anastasis was determined as described previously (Cifone and Fidler, 1980) with some modifications. Briefly, the cells were harvested by trypsinization. A total of 3×10$^3$ cells were resuspended in 1.5 ml of complete cell culture medium containing 0.3% agarose. The suspensions were cultured in single wells of six-well cell culture plates (Nunc) above a layer of solidified 0.5% agarose in the medium. After incubation at 37° C. under an atmosphere of 5% CO2/95% air for 5 wk, plates were stained with 0.5 ml of 0.005% crystal violet solution (Sigma-Aldrich) for 1 h before being subjected to microscopy.

New RNA Detection.

For newly synthesized RNA detection, cells were incubated in the presence of 50 μM 4-thiouridine (s4U; Sigma-Aldrich) for 1 h and total RNA was extracted by TRIzol (Invitrogen). The RNAs were then subjected to biotinylation as described (Zeiner et al., 2008). The biotin-labeled RNAs were agarose electrophoresed, transferred to nylon membrane (Bio-Rad) with Trans-Blot SD DNA/RNA Blotting Kit (Bio-Rad), and then detected by chemiluminescence using LightShift Chemiluminescent EMSA Kit (Pierce, Rockford, Ill.).

Microarray and Gene Expression Data Analysis.

Mouse primary liver cells were treated with 4.5% ethanol for 5 h (R0) and then washed and cultured in fresh medium for 3 (R3), 6 (R6), 24 (R24), and 48 (R48) h. The untreated cells were used as control (Ctrl). Total RNA was isolated and purified by RNeasy Mini Kit (Qiagen, Cologne, Germany). As a first level of quality control, to detect possible batch effects or sample outliers, we performed principal component analysis with Partek Genomics Suit 6.5 (Partek, St. Louis, Mo.) on log 2-normalized signal values for all samples; biological replicate samples were observed to cluster together. Furthermore, an analysis of variation was run on all data, including variables for cell sample, batch, and error, in which analysis also showed an excellent ratio of signal (biological variation) to noise (batch and error). The RNA was subjected to reverse transcription using SABiosciences C-03 RT2 First Strand Kit (SABiosciences-Qiagen, Frederick, Md.). These cDNA samples were analyzed on the Illumina MouseWG-6 v2.0 Expression BeadChip (Illumina, San Diego, Calif.).

Processed Illumina signal value data were imported into the Partek and Spotfire DecisionSite 9.1 (TIBCO, Palo Alto, Calif.) platforms for evaluation for expression fold change at the gene level between time points and for fold change across time when compared with a common starting point. First, all signal values were converted into log 2 space and quality control tests run to ensure data integrity. Signals for the three biological replicates at each time point were taken together for comparison to other time points; Student's t test used to determine statistical significance as p values, and fold change was based on averaged values. For our time-course analysis, all time points were compared with time point R0, the time at which ethanol treatment ended. Functional Gene Ontology (The Gene Ontology Consortium, www.geneontology.org) and pathway analyses were run with Spotfire's Gene Ontology Browser and Ingenuity Pathway Analysis (Ingenuity Systems, www.ingenuity.com) software, respectively.

qRT-PCR.

Total RNA was isolated and purified by RNeasy Mini Kit (Qiagen, Cologne, Germany), and 1.5 μg of the total RNA was reverse transcribed into cDNA via the M-MLV reverse transcriptase (Invitrogen with oligo-dT as primer. RT-PCR was performed on an IQ5 machine (Bio-Rad) using SYBR GreenER qPCR SuperMix (Invitrogen) in 25 μl of reaction with the following PCR cycle parameters: 10 min at 95° C. (pre-denaturation and hot start); 40 cycles of 35 sat 95° C.; 35 s at 58° C.; 30 s at 72° C. (denaturation/annealing/amplification). The following primers were used for detection of their corresponding mRNA. Bcl2 forward primer sequence, 5'-CCT GTG GAT GAC TGA GTA CC-3' (SEQ ID NO:1); reverse primer sequence, 5'-GAG ACA GCC AGG AGA AAT CA-3' (SEQ ID NO:2) (Sigma-Aldrich). Xiap forward primer sequence, 5'-CTG AAA AAA CAC CAC CGC TAA C-3' (SEQ ID NO:3); reverse primer sequence, 5'-CTA AAT CCC ATT CGT ATA GCT TCT TG-3' (SEQ ID NO:4). Mdm2 forward primer sequence, 5'-CGG CCT AAA AAT GGC TGC AT-3' (SEQ ID NO:5); reverse primer sequence, 5'-TTT GCA CAC GTG AAA CAT GAC A-3' (SEQ ID NO:6). Hsp90aa forward primer sequence, 5'CTC CAA TTC ATC GGA CGC TCT G 3' (SEQ ID NO:7); reverse primer sequence, 5' TCA AGT CGG CCT TGG TCA TTC C 3' (SEQ ID NO:8). Gapdh forward primer sequence, 5'-TGC CTC CTG CAC CAC CAA CT-3' (SEQ ID NO:9); reverse primer sequence, 5'-CGC CTG CTT CAC CAC CTT C-3' (SEQ ID NO:10). All RT-PCR assays were completed in triplicate, and the threshold cycle of each reaction was converted to DNA equivalent by reading against its corresponding standard curve generated by amplifying dilutions of cDNA containing the relevant target sequences. The relative mRNA expression levels of the target genes were normalized to the mean of Gapdh, which served as the internal control.

Inhibitor Treatment.

Immediately after removal of apoptotic inducers, specific inhibitor targeting BCL-2 (ABT 263, 1 μM; Selleck Chemicals, Houston, Tex.), XIAP (Embelin, 20 μM; Sigma-Aldrich), MDM2 (MDM2 inhibitor, 20 μM; Sigma-Aldrich), or HSP90 (17-allylaminogeldanamycin, 0.5 μM; Sigma-Aldrich) was applied to the cells together with fresh culture medium. A mock experiment was also performed in the untreated cells.

Statistics.

Statistical comparison was performed using two-tailed (unless stated otherwise) Student's t test (except in microarray and gene expression data analysis, as described in the corresponding section). Differences were considered to be significant when the p value was <0.05.

Example 1: Reversal of Apoptosis after Caspase Activation

Figure 2:
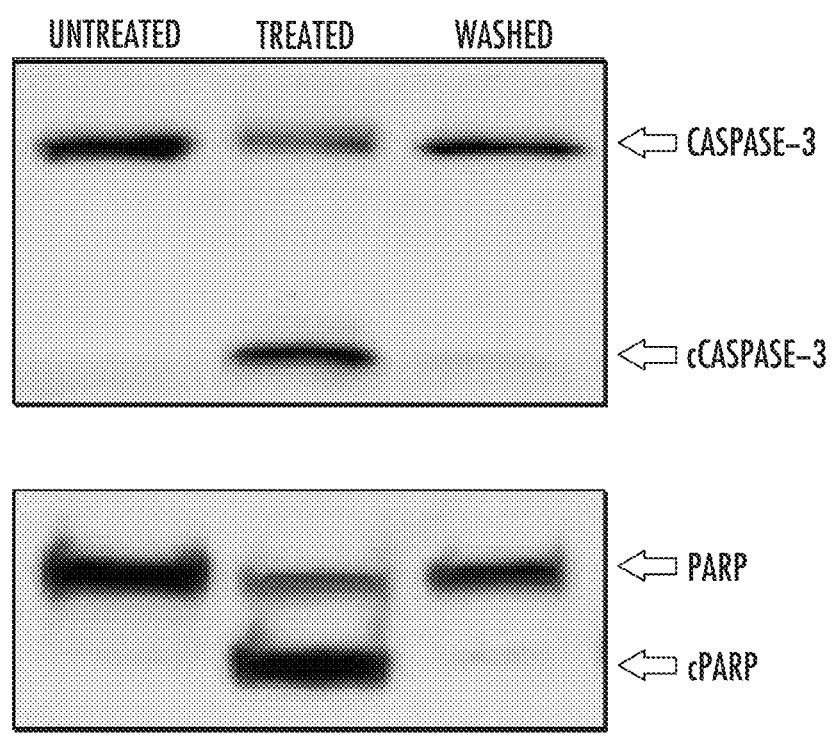
FIG. 2 illustrates reversal of apoptosis in liver cells after caspase-3 activation. Western blot analysis on the total cell lysate to detect caspase-3, and its substrate PARP. cPARP=cleaved form.

The Present Inventors discovered that apoptotic cells can survive and reverse apoptosis, even after passing through critical checkpoints previously described to be points of no return including caspase-3 activation. In time-lapse, live-cell movies, cells that are induced to undergo apoptosis exhibit the classic morphological manifestations including cell shrinkage, nuclear condensation, and membrane blebbing. See FIG. 1a-1c. Strikingly, following washing away of the inducer, the same cells recover normal morphology. See FIG. 1d-1f. This is not the behavior of a few "escapers" as >90% of cells exhibit both morphological and biochemical hallmarks of apoptosis and the reversal. When they reverse apoptosis, cells resume production of pro-caspase-3 and full-length PARP and the cleaved forms disappear. See FIG. 2.

Figure 3A:
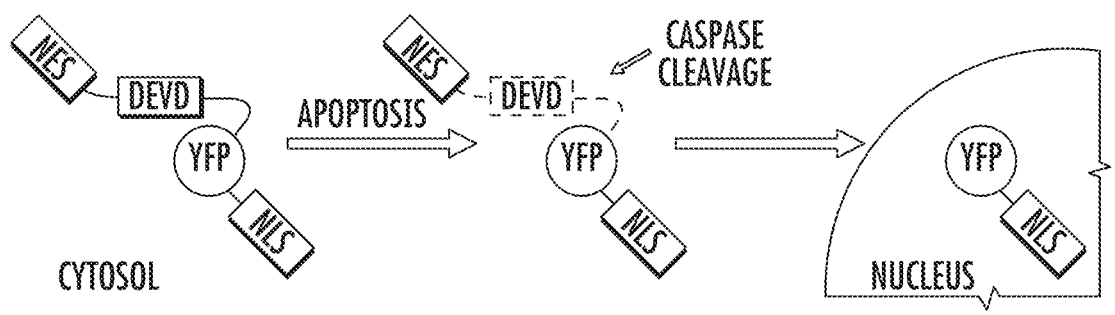
FIG. 3A-3B shows reversal of apoptosis after caspase activation in HeLa cells.
Figure 3B:
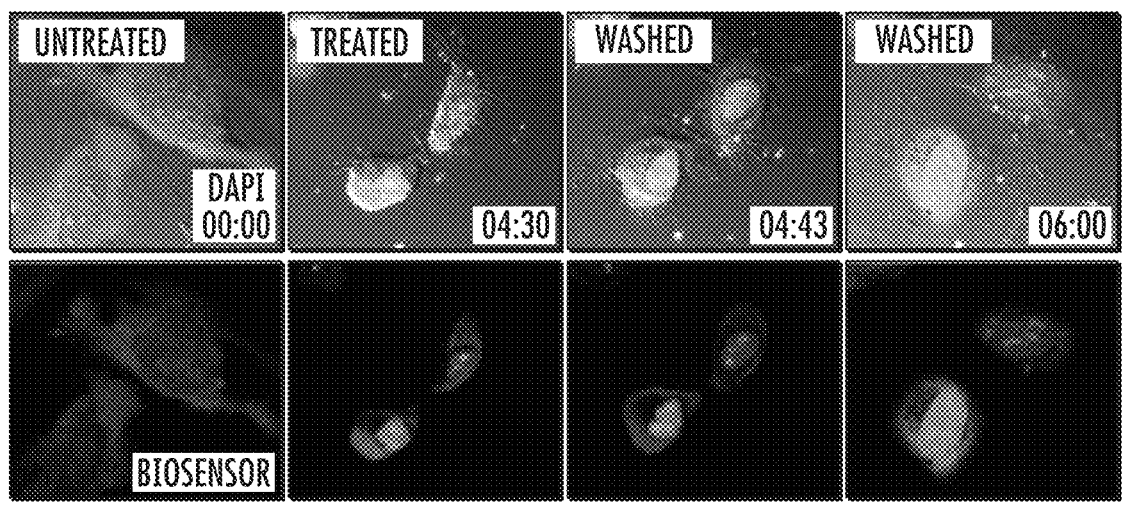
Figure 4A:
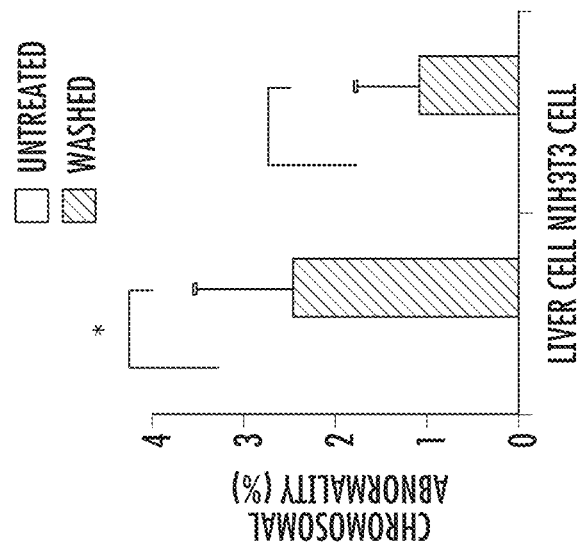
FIG. 4A-4C describes genetic alterations in liver and NIH3T3 cells after reversal of apoptosis.
Figure 4B:
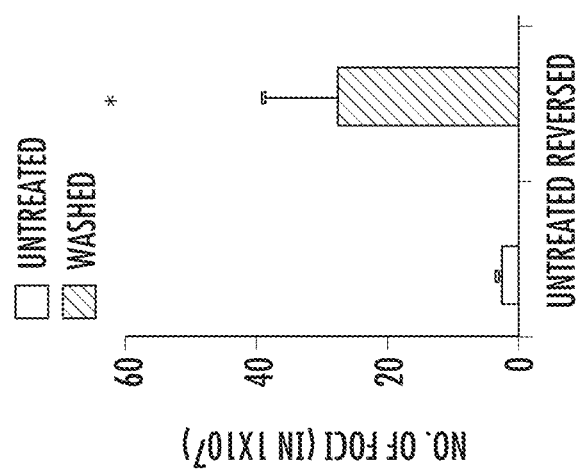
Figure 4C:
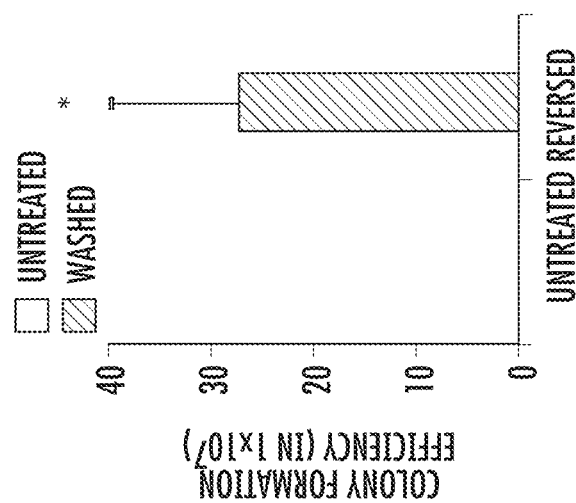
Figures 5A, 5B, 5C, 5D, 5E:
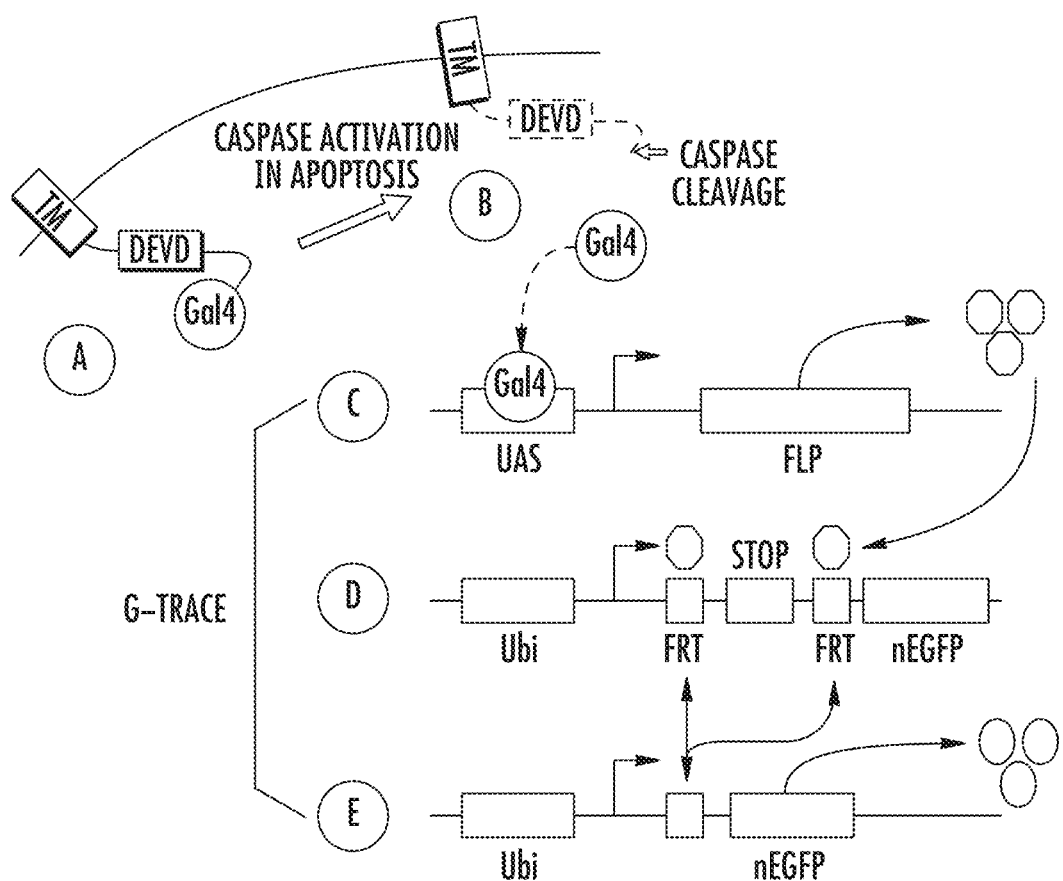
FIG. 5A-5E shows the design of a biosensor for detecting reversal of apoptosis in vivo, using *Drosophila* as a model system.
Figure 6:
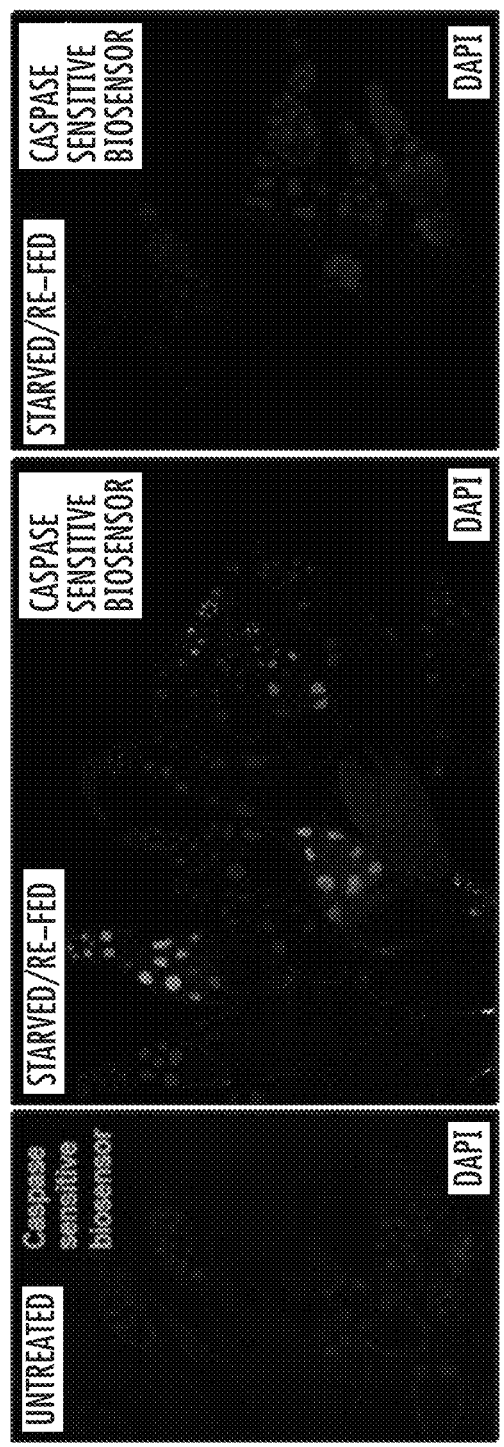
FIG. 6 shows reversal of apoptosis after protein starvation in *Drosophila* ovary. Female flies were starved (8% sucrose in 1% agar) for 3 days, and then were re-fed with yeast fly food. Merged images of egg chambers at the ovary: caspase biosensor (GFP) and nuclei (blue) were visualized by fluorescence.

In living HeLa cells expressing a biosensor for caspase activity, induction of apoptosis results in caspase-mediated cleavage and nuclear translocation of GFP. See FIG. 3. Washing away of the inducer results in morphological recovery of the cells with nuclear GFP demonstrating recovery from caspase activation at the single cell level. During apoptosis, the vast majority of cells exhibit DNA double strand breaks. During reversal, DNA repair is induced and much of the damage is reversed. However in some cells chromosomal abnormalities persist. See FIG. 4a. Signs of oncogenic transformation, including focus formation (FIG. 4b) and colony formation in soft agar (FIG. 4c) are also observed, possibly due to DNA damage generated during the dying process.

Example 2: Design of Anastasis Biosensor

The present inventors' observation that cultured cells can reverse apoptosis and survive raises the critical question as to whether this process can occur in an animal. To test for anastasis in living animals, an in vivo biosensor was developed that permanently marks cells that experience transient caspase activation, which is one of the key hallmarks of apoptosis, and has been generally assumed to be the point of no return. See Chipuk et al., 37 Mol. Cell. 299-310 (2010); Taylor et al., 9 Nat. Rev. Mol. Cell. Biol. 231-41 (2008); and Riedl et al., 5 Nat. Rev. Mol. Cell. Biol. 897-907 (2004).

The fruit fly *Drosophila melanogaster* was chosen as the first animal model because of the sophisticated repertoire of genetic tools, low cost, and rapid generation time. In this embodiment, the *Drosophila* biosensor comprises of two elements: a caspase-activatable form of the transcription factor Gal4, and an existing technique known as G-TRACE, which converts transient Gal4 activity into permanent expression of green fluorescent protein (GFP). See Evans et a., 6 NAT. METHODS 603-5 (2009). Gal4 is a transcriptional activator that must be present in the nucleus in order to bind to Upstream Activating Sequences (UAS), thereby stimulating expression of an adjacent gene. See FIG. 1. A Gal4 protein that is tethered to the plasma membrane via a caspase-cleavable linker peptide and a transmembrane domain was constructed. Upon executioner caspase activation, the DEVD peptide is cleaved, Gal4 is released and translocates to nucleus. This activates G-TRACE, causing a recombination event that results in permanent expression of GFP. Transgenic flies expressing caspase-inducible Gal4 and G-TRACE were generated. A control biosensor was also generated in which the caspase cleavage site was mutated.

In one embodiment, the caspase-activatable form of the transcription factor Gal4 comprises 3 elements: 1) N-terminal (trans-membrane domain) region of mouse CD8 (MCD8), 2) a caspase-cleavable linker peptide from the *Drosophila* inhibitor of apoptosis protein 1 (DIAP1) with BIR1 domain to enhance recognition by caspases, and 3) transcription factor Gal4. The actual cleavage site of DIAP1 (DQVDNN) was modified to DQVDGV as described (Bardet et al., 105 PROC. NATL. ACAD. SCI. U.S.A. 13901-5 (2008)) to prevent degradation of the cleaved product by the N-end rule pathway. See Ditzel et al., 5 NAT. CELL. BIOL. 467-73 (2003). A mutated fragment of DIAP1 that cannot be cleaved (DQVANN) served as negative control. These DNA fragments were ligated to form MCD8-BIR1-Gal4, which was then cloned into a vector with Ubiquitin promoter (Ubi) for fly injection to generate caspase-activatable Gal4 flies. The existing G-TRACE flies were cloned as described. The Gal4 and G-TRACE flies were crossed so that their progenies have both of the Gal4 and G-TRACE elements.

To test the biosensors, female flies were starved, a treatment that is known to induce apoptosis of egg chambers, and then re-fed them. Egg production rapidly resumes once the flies are re-fed with protein (Drummond-barbosa et al., 231 DEV. BIOL. 265-78 (2001)), however it is not known if egg chambers that initiate apoptosis can reverse that process and survive or if instead apoptotic egg chambers are removed by phagocytosis. Following starvation and re-feeding of transgenic flies bearing the caspase-inducible Gal4 and G-TRACE, approximately 3% of egg chambers expressed GFP (n>300), indicating that they had survived transient caspase activation. This corresponds to about 30% of the egg chambers that initiate apoptosis, since not all egg chambers die in response to starvation. Early stage chambers simply arrest development. Drummond-barbosa et al., 231 DEV. BIOL. 265-78 (2001). In flies that were not starved <0.3% of egg chambers expressed GFP (n>300). In flies expressing the caspase-insensitive control biosensor, 0% of egg chambers expressed GFP before or after starvation (n>300). See FIG. 2. These results reveal that the biosensor is effective and that reversal of apoptosis can occur in living animals under conditions that are known to induce apoptosis.

Example 3: Characterization of Anastasis In Vivo

The present inventors propose that anastasis is a mechanism to allow cells and organisms to survive transient insults. To test for anastasis, flies will be subjected to transient perturbations that are known to induce apoptosis. For example, adult flies are subjected to heat-shock (38° C., 30 min) or cold stress (−3° C., 2 hr), both of which induce apoptosis in muscle. A temperature-sensitive (ts) mutation in the gene coding for dynamin (shibiretsi) allows normal endocytosis to occur at <22° C., but not at restrictive temperatures (>31° C.). At non-permissive temperatures, blockade of synaptic transmission leads eventually to neural degeneration. A ts mutation in the tefu gene, which encodes *Drosophila* ATM, functions normally at <22° C.; however apoptosis occurs in imaginal disc cells at or above 31° C. Following induction of apoptosis, standard apoptosis assays is performed including immunostaining for the activated form of effector caspase and TUNEL labeling for DNA damage to confirm that apoptosis occurs in the expected tissues. Flies from the same group are then allowed to recover at the permissive temperature. Skeletal muscle is examined at different time points during recovery to test for GFP expression from the biosensor, which marks surviving cells that have experienced caspase activation. Two types of controls are used: 1) animals that are not subjected to stress and 2) animals that express the caspase insensitive form of membrane-tethered Gal4 and are subjected to stress.

A particularly intriguing possibility is that anastasis can rescue dying adult neurons exposed to transient adverse environmental conditions. The *Drosophila* compound eye is a classic genetic model for studying mechanisms associated with neuronal cell fate specification, differentiation, degeneration and survival. Compared with other organs, the eye offers a unique opportunity for imaging because it allows direct and continuous observation of photoreceptor cells in the same live animals. Photoreceptor cells in the compound eye die under environmental stress such as continuous exposure to moderate room lights, resulting in retinal degeneration. Intriguingly, if photoreceptor cells are returned to a normal light/dark cycle within the first few days of constant light, they can recover. The present inventors propose that this might represent a physiological example of anastasis, allowing the animal to spare precious neurons and their ability to see. Here, the present inventors propose to test whether photoreceptor cells exposed to constant light undergo anastasis when the light/dark cycle is restored. The biosensor is combined with in vivo imaging. Using this approach, the same group of photoreceptor cells can be directly visualized and continually monitored with single-cell resolution in the same fly over many days. As controls, animals that are not subjected to stress and animals that express the caspase insensitive form of membrane-tethered Gal4 and are subjected to stress are again used.

The percentage of cells expressing GFP from the treated and control groups of animals is compared. Only cells that have experienced executioner caspase activation and yet survive, express GFP. Therefore, the present inventors do not expect to detect dying or dead cells but rather only those cells that reverse the process and survive. The present inventors also do not expect to detect basal caspase activity in normal cells. *Drosophila* border cells, for example, require some initiator caspase activity for normal Rac-mediated migration, but do not require effector caspase activity or exhibit any other hallmarks of apoptosis. Because the biosensor is not active in border cells, the present inventors are confident that it is not overly sensitive. It is not expected to see GFP-positive cells in some or all of the conditions in which there is induced apoptosis and phenotypic recovery and this will indicate how prevalent anastasis is in vivo.

The preliminary data suggest that the sensor is tuned properly to detect actual anastasis events rather than basal caspase activity or noise. However, if reporter activation in tissues other than the ovary following transient apoptotic stimuli is not detected, multiple copies of the caspase sensitive Gal4 transgene (and the negative control) will be combined to increase sensitivity. If GFP expression is still not observed in tissues following transient induction of apoptosis, the sensitivity can be further enhanced by including additional copies of the DEVD sequence in the biosensor. If anastasis is still not detected, these tissues probably do not undergo reversal of apoptosis or the appropriate cell types or stimuli have not been identified, and others will be tested. It is possible that, for reasons that are not obvious at the moment, anastasis could turn out to be more prevalent in mammalian cell types than insect cell types. Since anastasis has already been detected in multiple mammalian cell types and in fruit fly germ cells subjected to transient stress in vivo, the remaining embodiments should be unaffected by this result.

Example 4: Development of an Anastasis Biosensor in Mice

Figures 7A, 7B, 7C, 7D:
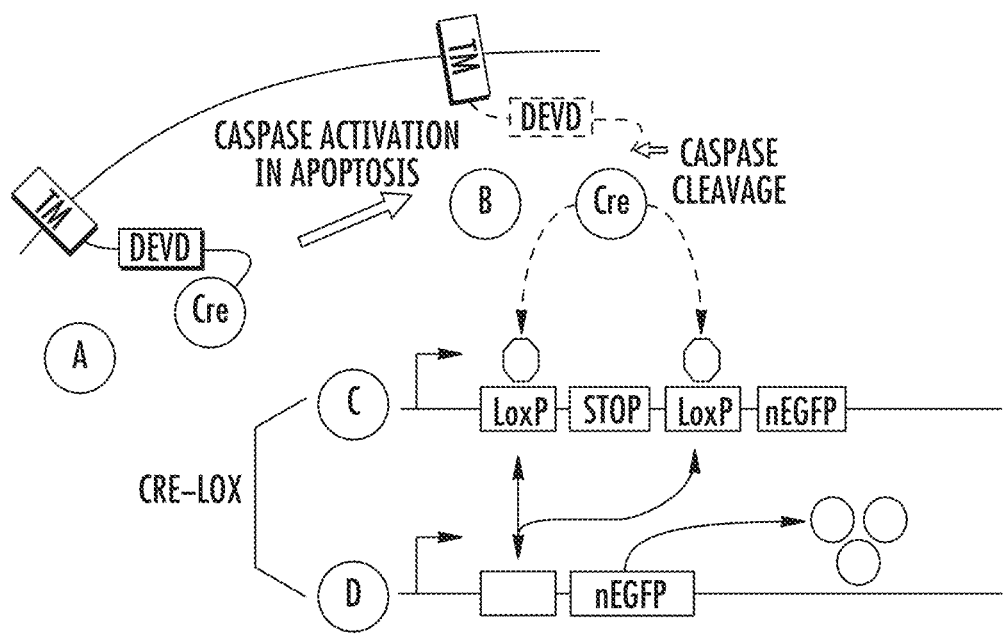
FIG. 7A-7D illustrates the design of a biosensor to detect reversal of apoptosis in cancer cells in mouse recurrence model system.

The discovery that a variety of cultured cell lines and primary liver cells undergo anastasis raises the intriguing possibility that this mechanism exists in order to protect cells that are difficult to replace such as neurons and heart cells. To test the hypothesis that mammalian neurons and heart cells can undergo anastasis, a mouse version of the anastasis biosensor is developed using a strategy conceptually similar to the one used in *Drosophila*, as described in Example 1 above. In one embodiment, the mouse biosensor will comprise a ubiquitously expressed caspase-activatable form of the Cre recombinase (Cre) and existing mouse strains that express either a red or green fluorescent protein when a stop codon that is flanked by LOXP sites is eliminated by the Cre recombinase. See FIG. 7. Cells from mice bearing these two transgenes will permanently express the fluorescent protein if and only if they experience transient caspase activity and then survive. In a particular embodiment, transgenic mice expressing tamoxifen-inducible Cre ubiquitously will be utilized. See Badea et al., 23 J. NEUROSCI. 2314-22 (2003). In a simple cloning step, starting this such a construct, a Cre protein will be generated that is tethered to the plasma membrane via a caspase-cleavable linker peptide and a transmembrane domain instead of the tamoxifen-induction domain. Upon caspase activation, the peptide will be cleaved and Cre will be released and translocate to the nucleus. This will activate a recombination event that results in permanent expression of a fluorescent protein. As a negative control, a membrane-tethered Cre with a mutated caspase cleavage site is used so that it is not sensitive to caspase activity. Primary neurons and glial cells will then be isolated from brains of newborns and cardiac myocytes from the hearts. Apoptosis will be induced with ethanol as well as other inducers including calcium/streptolysin O, dimethyl sulfoxide, jaskplakinolide and paclitaxel. Following induction of apoptosis, the medium is changed, the cells allowed to recover, and the number of cells that survive and express the fluorescent protein are quantified.

Compared with other organs, the eye offers a unique opportunity for imaging because direct and continuous observation and tracking of photoreceptor cells in the living animals over time is possible. Previous studies show that in mammals, as in flies, photoreceptor cells undergo apoptosis in response to exposure to constant light. Interestingly, signs of apoptosis in the retina are reduced when the animals are returned to normal light cycles. However, it is not known if individual cells that have initiated apoptosis can recover of if the dead cells are cleared by phagocytosis. The biosensor mice will be used to track apoptotic photoreceptor cells, whether GRP appears in retinal neurons will be determined.

If expression is observed in cells following transient induction of apoptosis but not in control animals (untreated animals expressing the anastasis biosensor or treated animals expressing the caspase-insensitive sensor), then reversal of apoptosis is likely to be a physiological process in vivo. It is possible that primary cells will express the anastasis biosensor even without any treatment to induce apoptosis because it is possible that the process of isolating primary cells induces anastasis. During the harvesting procedure and over subsequent days in culture, it is typical for many cells to die whereas others live. It is possible that some or all of the living cells actually undergo anastasis. If this is the case, GFP positive cells will be observed in the primary cultures (but not in histological sections of preserved tissues). This result would provide strong evidence that anastasis is a property of normal cells. It might limit the ability to test whether these cells undergo anastasis in response to subsequent treatments, but brain slice preparations could be used, for example, in which cells remain in a more native setting.

The biosensor is likely to work since it is similar to the *Drosophila* sensor that appears to be tuned to the correct sensitivity. Nevertheless, if the mouse turns out to be too sensitive, and is activated by basal levels of caspase activity in normal tissues, a tamoxifen-inducible form will be made by adding the transmembrane domain and caspase cleavable linker to the existing tamoxifen-inducible Cre construct. In this way, the biosensor will not be expressed and thus not activated until we begin our experiment. If on the other hand the mouse sensor it is not sensitive enough, additional copies of the caspase cleavage site will be added. All of the elements of the biosensor have been tested, but if for any reason it does not work, whether primary neurons and/or heart cells undergo anastasis can still be tested. In this case, primary cells will be sparsely labeled by transfection with a fluorescent protein, and their morphology followed over time in primary culture. Mitochondria and nuclei can be labeled with vital dyes as have been done for primary liver cells (FIG. 1) and cell morphology can be monitored with DIC optics. Sparse labeling is useful for neurons in particular because they have to be cultured in very dense conditions. Based on published results, even without the biosensor, retinal cell apoptosis and its reversal as well can be followed, although the biosensor would yield more definitive results. If robust anastasis in cardiac myocytes or in neurons is not found, it may be that these cells are not intrinsically capable of activating this pathway. In this case, once the components of the molecular pathway becomes known, it would be of interest to identify drugs that activate the pathway in cells in which it is not naturally activated. Another possibility is that cells from newborn animals will undergo anastasis whereas cells from older animals will not. In this case, elucidation of the molecules involved may lead to strategies for reactivating this pathway that is otherwise lost with age.

Example 5: Novel Screening Strategy for Identifying Specific Molecular Regulators of Anastasis Apoptosis contributes significantly to liver injury, heart failure, and neurodegeneration in humans, mice and fruit flies. The present inventors have observed reversal of apoptosis, i.e. anastasis, in primary liver cells, astrocytes and heart cells, and therefore suggest that elucidation of the molecular mechanisms of anastasis could provide novel strategies and molecular targets to enhance tissue repair and treat or attenuate ischemic and/or degenerative diseases. The present inventors also found that cancer cells can undergo anastasis, suggesting this could be a mechanism by which they escape chemotherapy and evolve resistance. It is therefore extremely important to elucidate the molecular mechanisms involved. Because apoptosis involves not only the activation of caspases but subsequently activation of nucleases and massive destruction of cellular components, reversal of the process is likely to be complex. Pro-apoptotic proteins that have been activated by proteolytic cleavage such as caspase and PARP, must be degraded. In fact, cleaved (i.e., activated) caspase and PARP disappear. See FIG. 2. In addition, repair mechanisms are induced and full length caspase and PARP are resynthesized. However the full suite of mechanisms required for anastasis is not yet known. The goal of this experiment is to identify genes required for anastasis. Identification of genes required for anastasis but not for baseline cell survival will be the highest priority.

To gain insight into the molecular mechanisms regulating anastasis, it was first determined that new gene transcription is required and a time course microarray analysis was then carried out to identify genes that are up- or down-regulated during recovery. See FIG. 7. Among the up-regulated genes, enhanced expression of multiple known pro-survival genes was observed, including BCL-2 family members (Bag3, Bcl2 and Mcl1), the murine double minute (MDM2), and heat shock proteins (Dnajb1, Dnajb9, Hsp90aa1, Hspa1b and Hspb1). Moreover pharmacological inhibition of each class prevented anastasis. These results suggest that 1) many gene products are required for the process and 2) factors required for anastasis may represent reasonable drug targets. It was also found that X-linked inhibitor of apoptosis protein (XIAP), which is an E3 ubiquitin ligase that targets caspases for degradation, is likely to be functionally required for anastasis because a specific chemical inhibitor of XIAP inhibits reversal of apoptosis, at a concentration that does not induce apoptosis in untreated cells.

An exciting possibility is that there is a pathway of regulators of anastasis, some of which are specifically or primarily involved in this process. Many of the genes that are up- or down-regulated during anastasis are not well characterized. In addition, there may be proteins that are required for anastasis but that are not regulated at the level of transcription and thus, do not appear in the microarray data. Therefore, to identify genes that are functionally required for anastasis, the present inventors propose to carry out an unbiased shRNA screen. The highest priority for follow-up will be those genes that are required for anastasis, but not for baseline cell survival or general stress responses. Secondary screening assays will help determine which of the genes are general regulators of anastasis across many cell types and apoptosis inducers. Other secondary screens will allow the construction of a molecular pathway if one exists.

Figure 8:
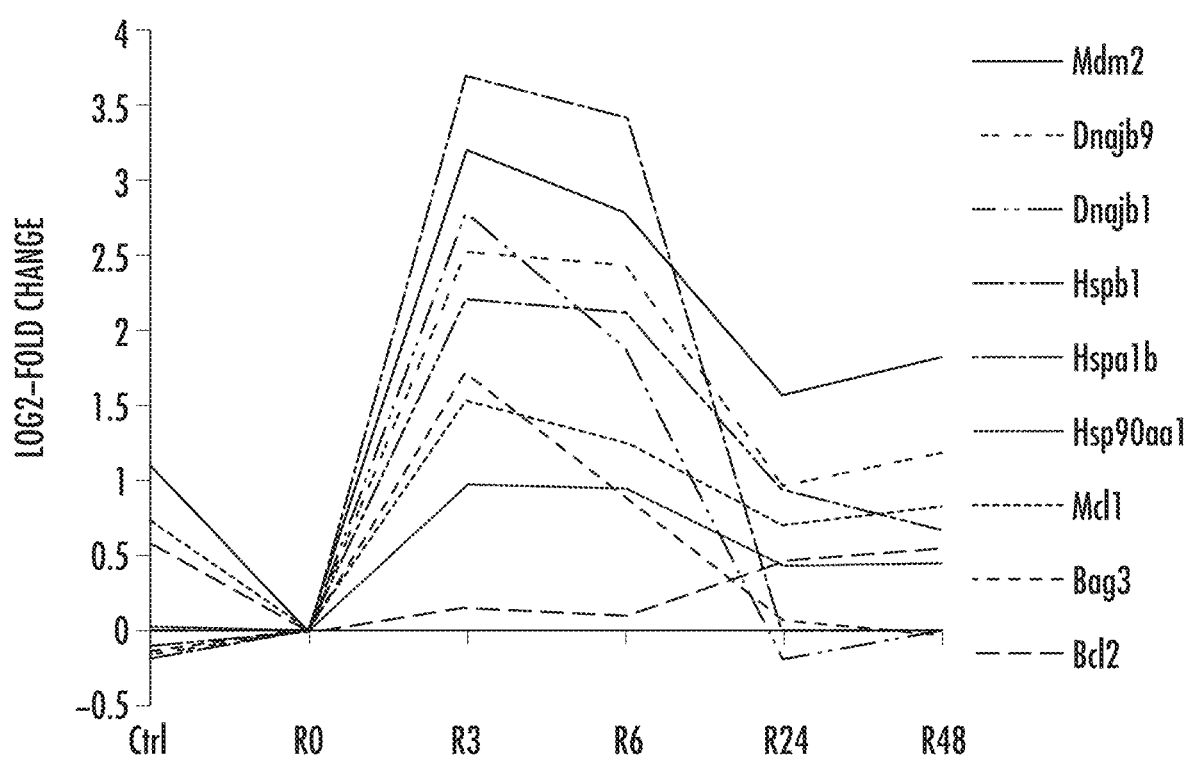
FIG. 8 presents the results from a time-course microarray study. Log 2-fold change of gene expression comparison between ethanol-induced apoptotic cells (RO) to the untreated cells (Ctrl), and the induced cells that were then washed and further cultured in fresh medium for 3 hours (R3), 6 hours (R6), 24 hours (R24) and 48 hours (R48).
Figure 9:
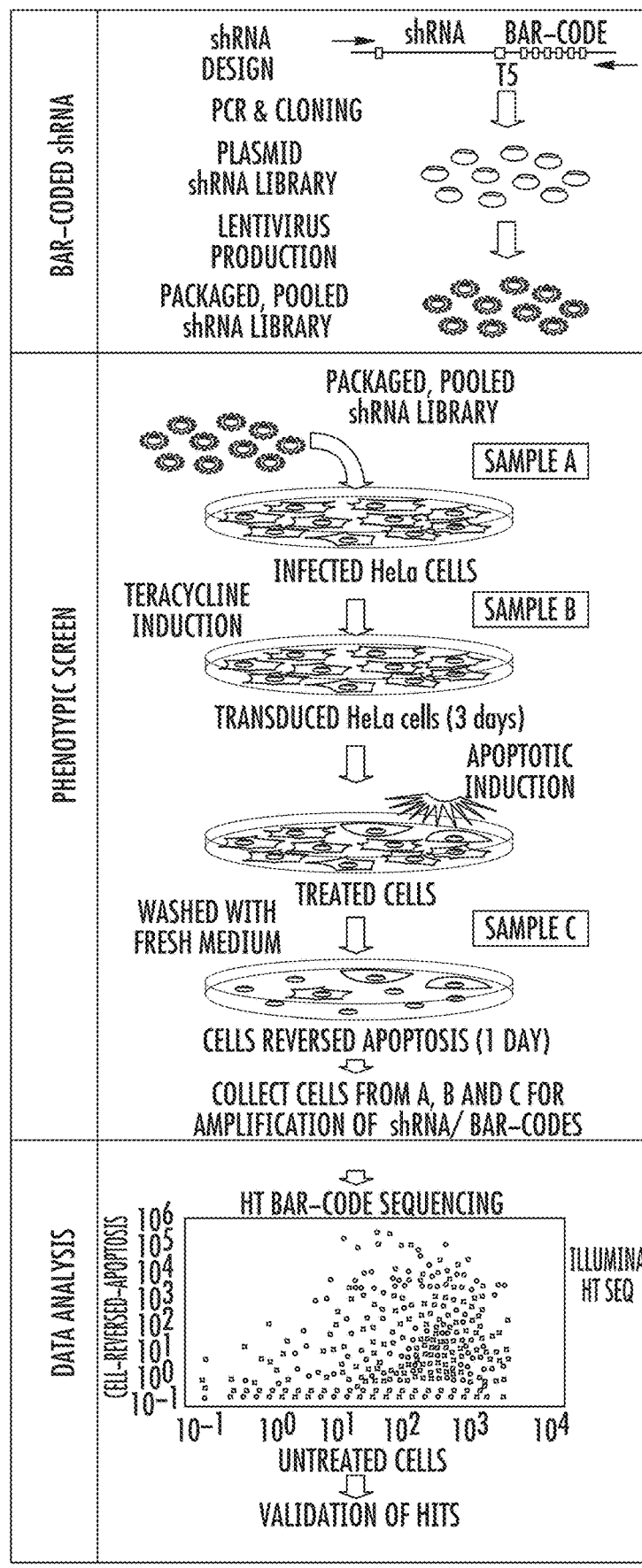
FIG. 9 illustrates the experimental strategy for identifying the genes required for reversing apoptosis by large scale shRNA screen.

To identify factors required for anastasis, a large scale RNA interference screen is performed in HeLa cells stably expressing the caspase biosensor. HeLa cells are used because of their very robust anastasis response and because they have served as an excellent model for many aspects of basic cell biology. A pooled lentiviral shRNA library from Cellecta will be introduced into the cells. See FIG. 8. After infection, expression of the shRNA is induced with tetracycline and the cells are incubated for three days to allow the shRNA to knock down expression of target proteins. Apoptosis is induced on day three. The inducer is removed three hours later and the cells are cultured for an additional day. Cell pellets are sent to Cellecta for Illumina high-throughput DNA sequencing to determine which shRNAs are present in 1) the starting population, 2) cells that survive 3 days shRNA treatment and 3) cells that survive induction and anastasis. Each shRNA plasmid contains a unique "barcode" sequence, allowing identification of the full set of shRNAs present in each cell population. shRNAs present in the starting population but not three days after shRNA induction will be those required for cell viability. shRNAs present three days after shRNA induction but absent after reversal of apoptosis will be those specifically required for anastasis but not for cell viability, and this will represent the highest priority class.

The following secondary screening criteria is then used to rescreen the candidates identified in the primary screen. See FIG. 8. Individual candidate genes are confirmed using multiple shRNAs against individual genes. More than one shRNA against a given gene will have to produce the same phenotype in order for the effect to be considered confirmed (5-6 different shRNAs per gene are present in the library). Confirmed positives are then used to test their requirement in response to multiple inducers of apoptosis. Because it is preferable to identify a core anastasis pathway, if there is one, candidate genes that are generally required for anastasis will be considered highest priority rather than those required only for the response to a specific inducer. Confirmed candidates are then tested against a panel of different cell types to determine if the gene is a cell-type specific regulator or a general regulator of anastasis. Again, highest priority is given to general regulators. It will then be determined whether an shRNA against a confirmed candidate blocks all aspects of anastasis or a subset of the process. The following assays are then performed: 1) live imaging in the presence of Hoechst and mitochondrial labeling (see FIG. 1) to follow the morphological signs of apoptosis and anastasis, 2) Western blotting to detect cleaved and full-length caspase and PARP, 3) comet assays and/or TUNEL labeling to detect damaged DNA, 4) staining to detect DNA double strand break repair.

An exciting possibility is that an entire regulatory pathway exists that could be deduced from these studies. If there are proteins dedicated to the anastasis pathway, one or more of these may be master regulators, disruption of which would prevent all aspects of anastasis. Other components may function downstream of the master regulators to control specific branches of the pathway, such as DNA repair, restoration of mitochondrial structure and function, or recovery of the cytoskeleton. Inhibition of such components would lead to a partial block of the process. So for example, cleaved caspase might disappear and full-length caspase reappear, but DNA repair might not occur in one particular gene knockdown whereas in another knockdown mitochondrial recovery might be specifically impaired. If there is an anastasis pathway, it will be of great importance because these proteins will represent a new class of potential drug targets.

In the event that the process of anastasis depends only upon genes that are also required for cell viability or general stress responses, the same type of secondary screening and pathway characterization will be carried out on this set of genes instead. In the proposed screen, those genes that are required for cell viability will be the set of viruses encoding shRNAs that are present in the infected cells prior to induction of expression of the shRNAs but absent three days later. To analyze the effect of these shRNAs on anastasis, expression of the shRNA will be induced for a shorter period of time prior to inducing anastasis and/or titrate the shRNA to find a concentration that does not kill the cell and then assay the effects on anastasis as described above.

One of the most exciting implications of the discovery of reversal of apoptosis is that it may offer a whole new set of drug targets for the treatment of a great number of diseases including heart failure, cancer, neurodegenerative disease, and possibly to facilitate tissue repair and homeostasis. The assays described here could in principle be used for screening drugs, such as the collection of drugs that have already passed FDA phase I safety trials, which is available at Johns Hopkins School of Medicine in the High Throughput Screening Center.

Figure 10A:
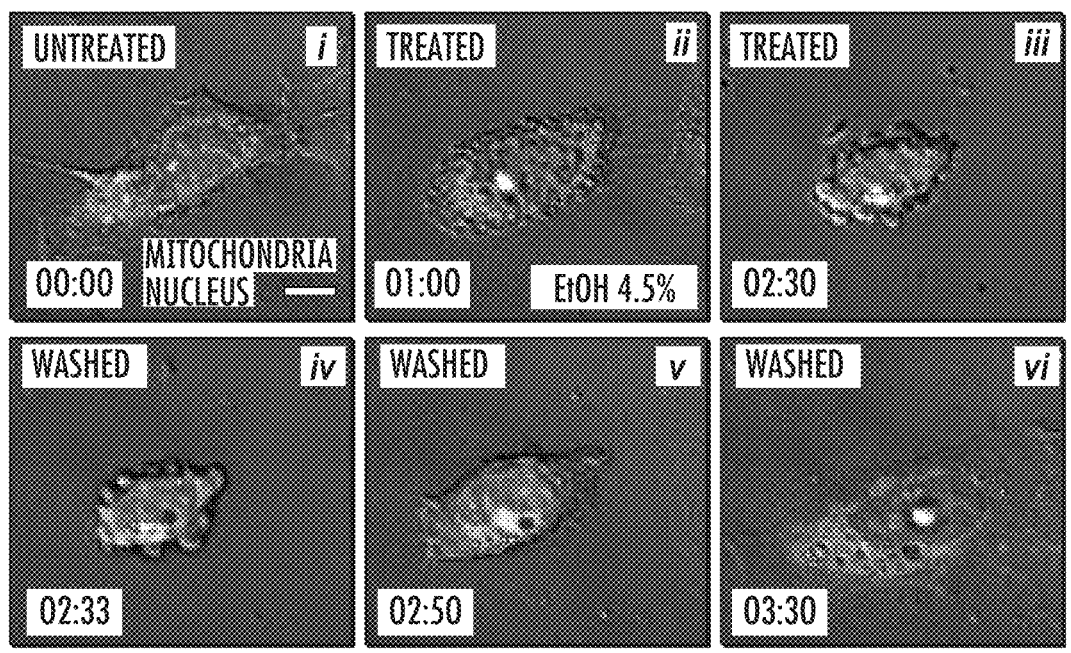
FIG. 10A-10H: Reversibility of apoptosis in primary mouse liver, NIH 3T3, and HeLa cells.
Figure 10B:
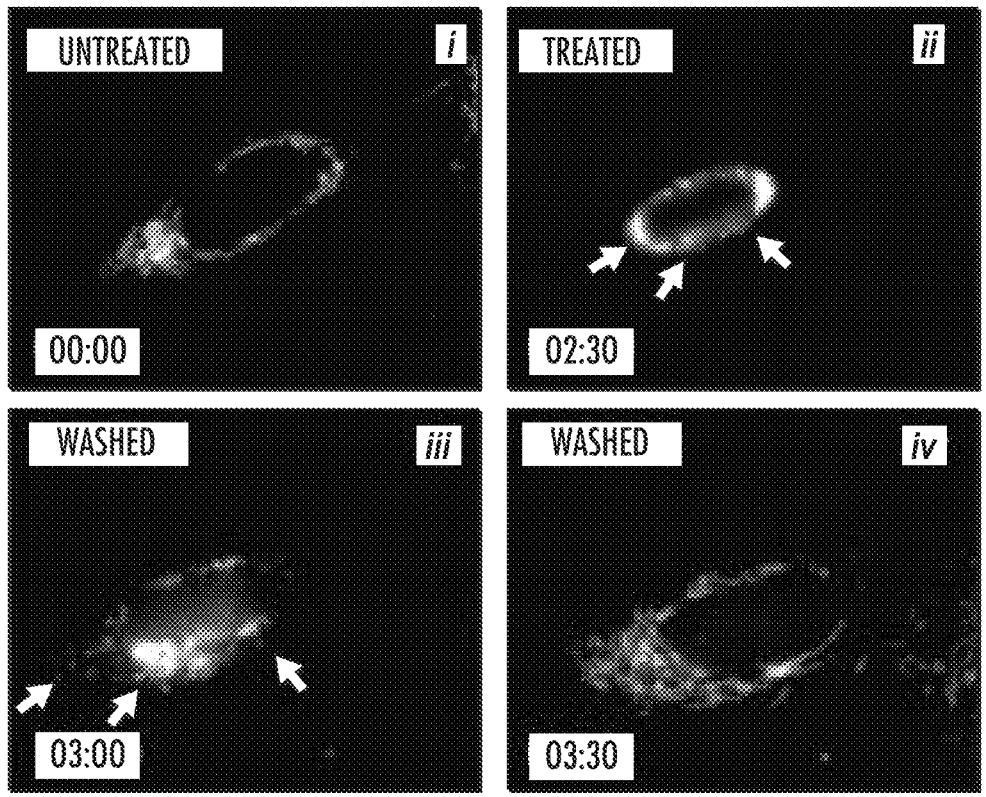
Figure 10C:
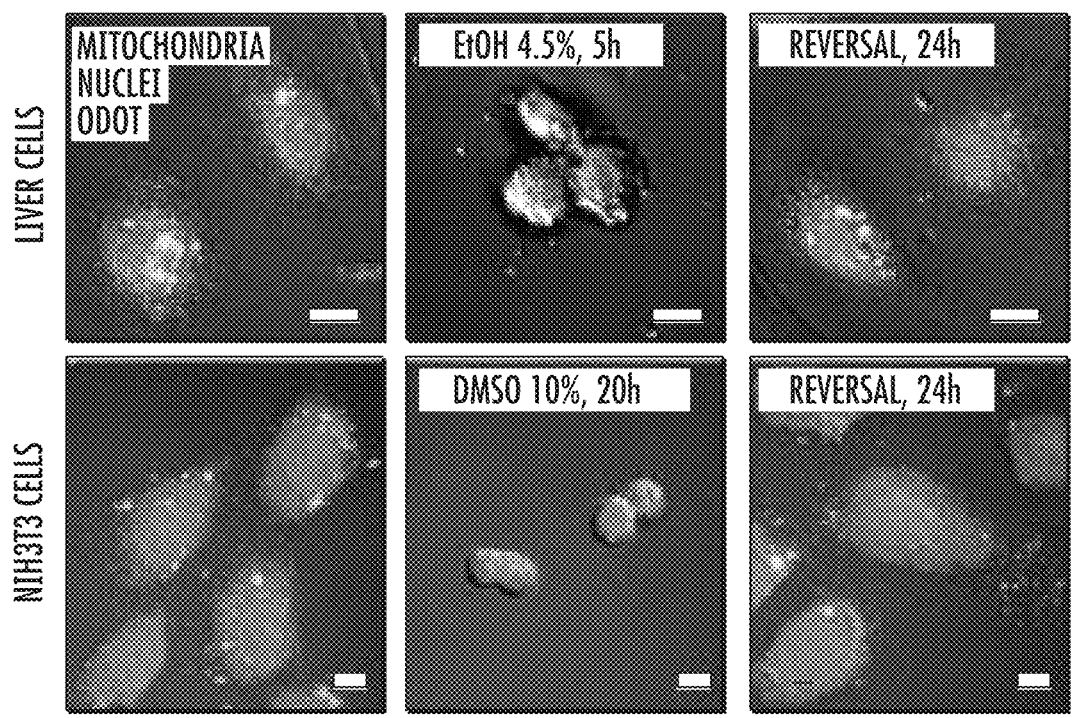
Figure 10D:
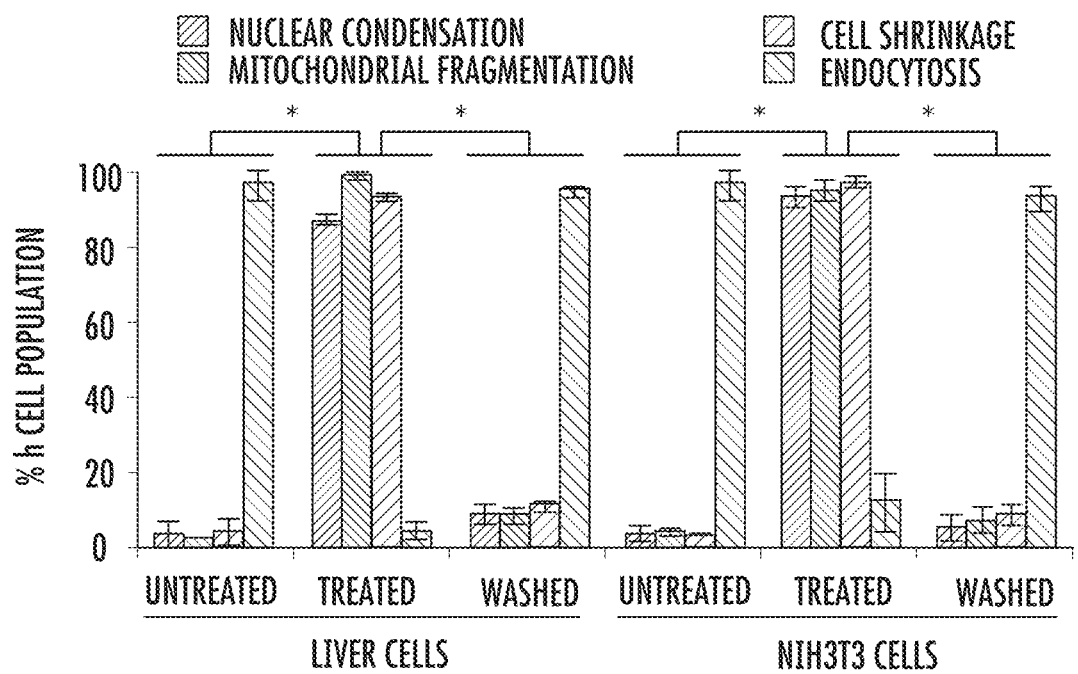

Example 6: Dying Cells Recover from Execution Stage of Apoptosis after Removal of Apoptotic Stimuli To test directly whether apoptosis is an irreversible process, we exposed cells to an apoptotic inducer until they showed typical hallmarks of apoptosis and then washed the inducer away. Untreated healthy cells spread on the substrate (FIG. 10Ai) and contained filamentous mitochondria that extended throughout cytoplasm (FIG. 10Bi). After exposure to 4.5% ethanol for 2.5 h, liver cells displayed morphological hallmarks of apoptosis, including cell shrinkage, plasma membrane blebbing, nuclear condensation (FIG. 10A, ii and iii), and altered mitochondrial morphology (FIG. 10Bii). These are well-recognized signs of effector caspase activation and define the execution stage of apoptosis (Taylor et al., 2008; Kroemer et al., 2009). Of interest, time-lapse live-cell fluorescence microscopy revealed that, upon washing, the same cells that had exhibited the morphological hallmarks of apoptosis recovered normal morphology (FIG. 10, A, iv-vi, and B, iii and iv), ruling out the interpretation that the apparent recovery represented cells that failed to respond to the inducer in the first place.

The reversal of the signs of apoptosis occurred in the vast majority of both primary liver and NIH 3T3 cells (FIGS. 10, C and D). After exposure to 4.5% ethanol for 5 h, >80% of liver cells shrank and displayed morphological hallmarks of apoptosis, and >90% of NIH 3T3 cells exhibited multiple hallmarks of apoptosis in response to 10% dimethyl sulfoxide (DMSO) for 20 h (FIG. 10D). Strikingly, >90% of both cell types reversed all signs of apoptosis after removal of the inducer for 24 h (FIG. 10D). The survival of cells was further assessed by their ability to take up Quantum Dots (Jaiswal et al., 2003) through endocytosis, which was abolished during ethanol induction and recovered following washing (FIGS. 10, C and D). Moreover, time-lapse microscopy of >30 living cells in a single field showed morphological recovery of the majority of them after removal of the apoptotic stimulus (data not shown). In contrast, virtually all cells died when they were left in the inducer (data not shown).

Figure 10E:
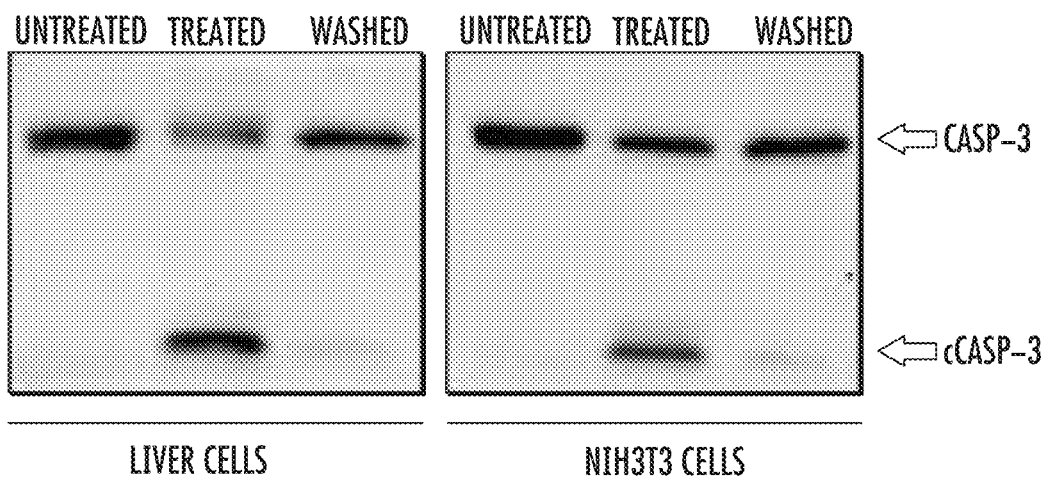
Figure 10F:
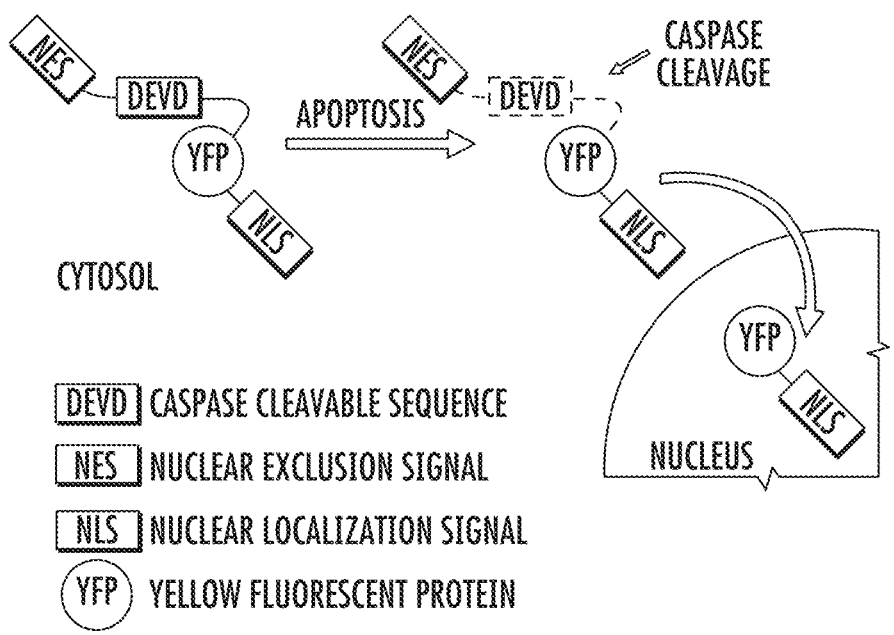
Figure 10G:
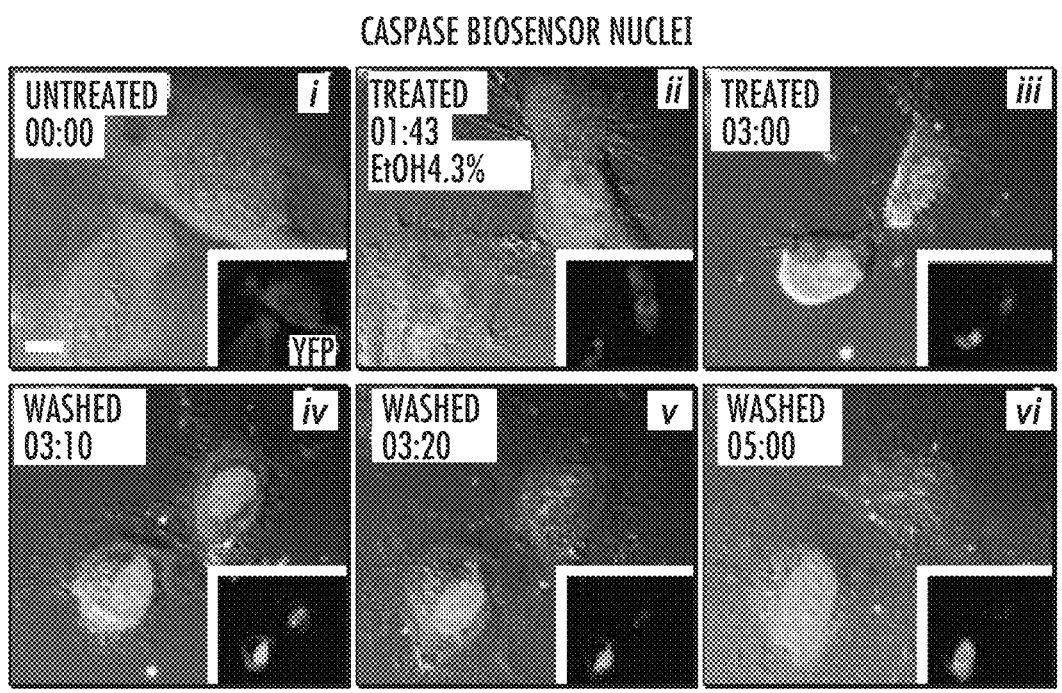
Figure 10H:
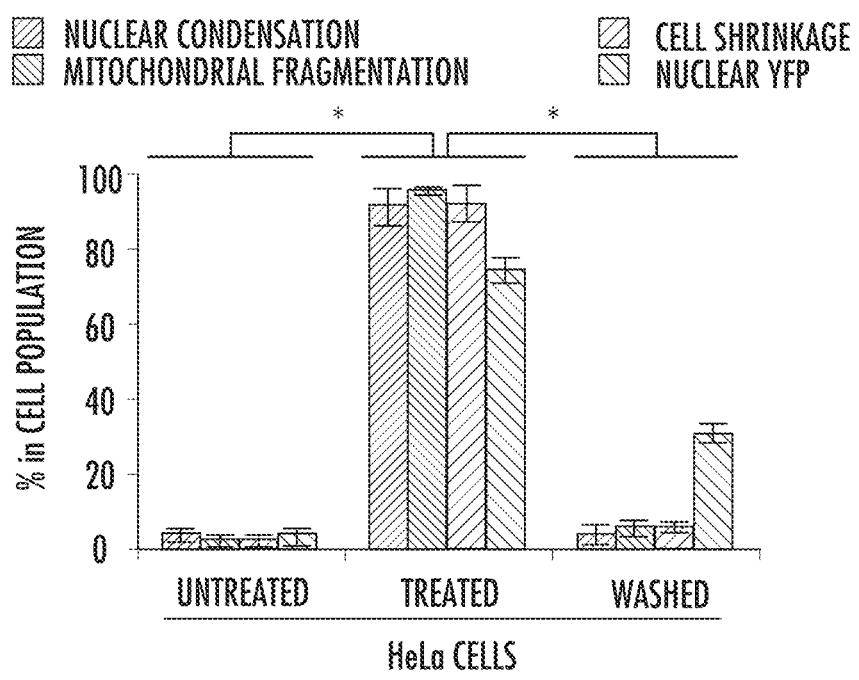
Figure 11A:
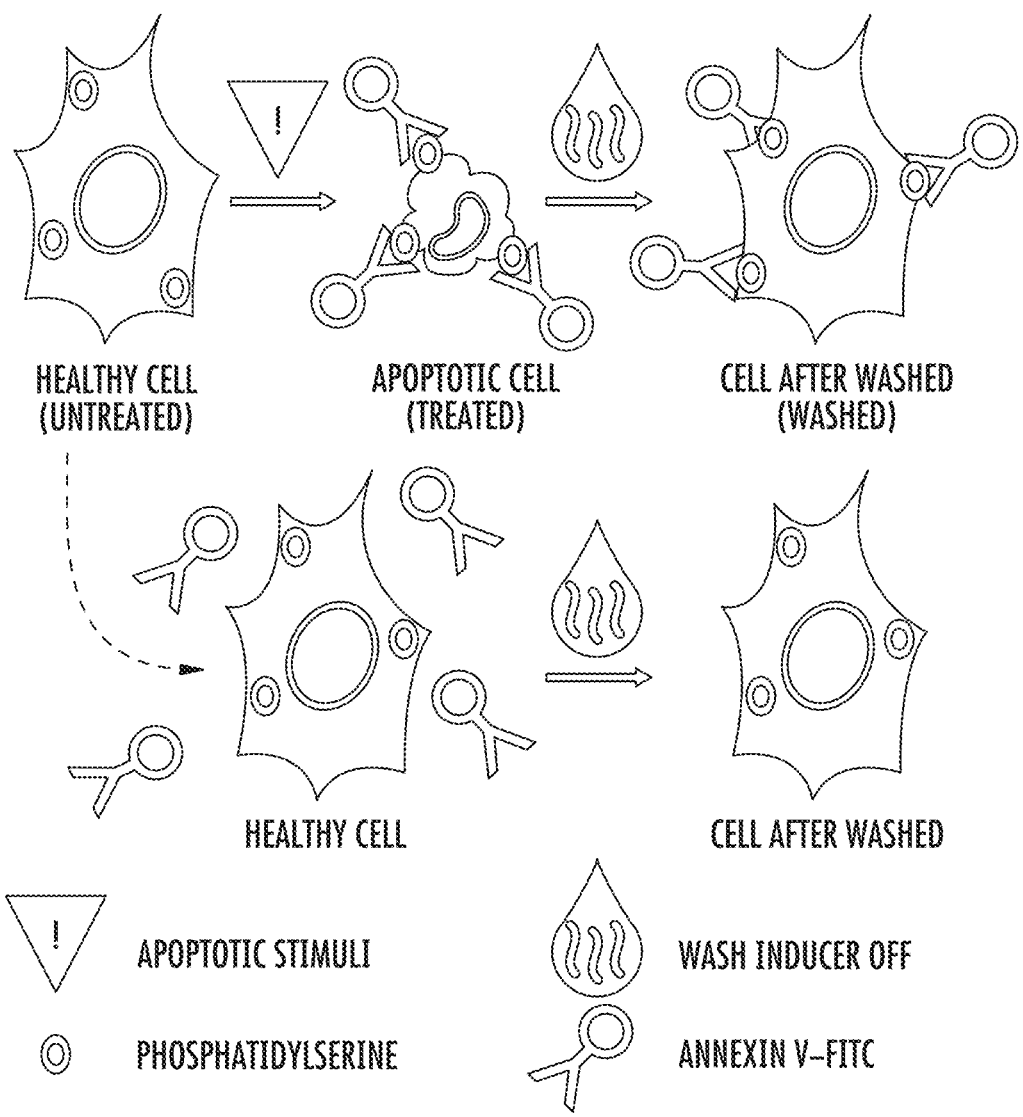
FIG. 11A-11E: Reversibility of apoptosis in primary rat heart cells, ferret brain cells, and primary mouse macrophages.
Figure 11B:
Figure 11C:
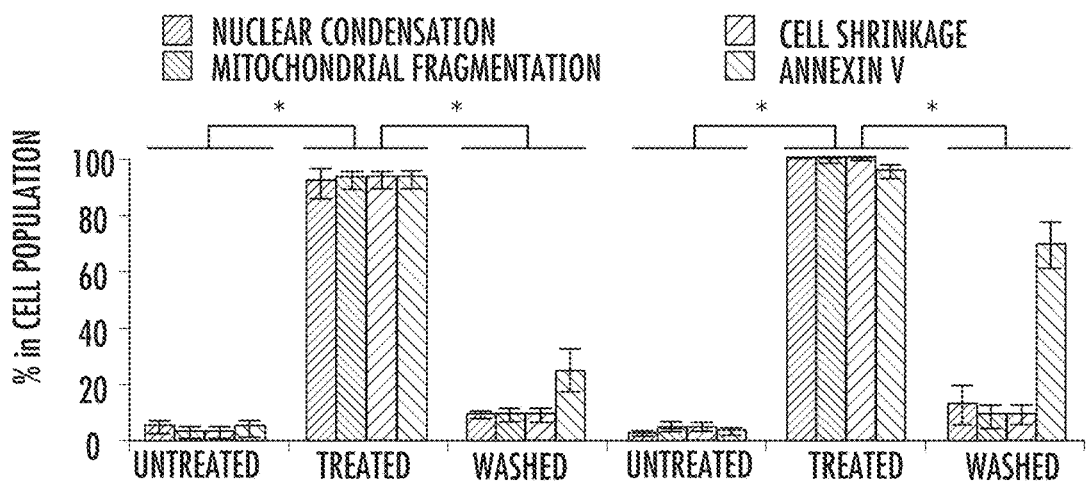
Figure 11D:
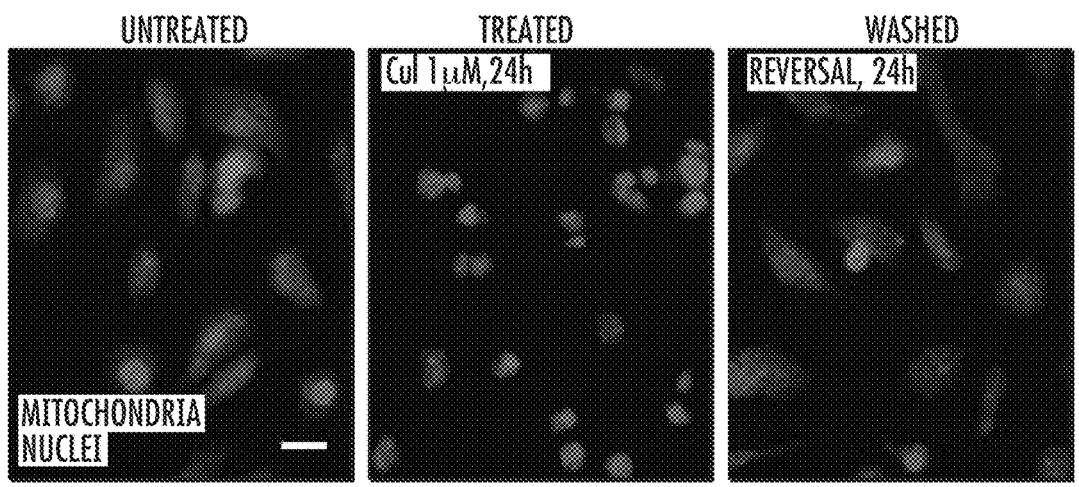
Figure 11E:
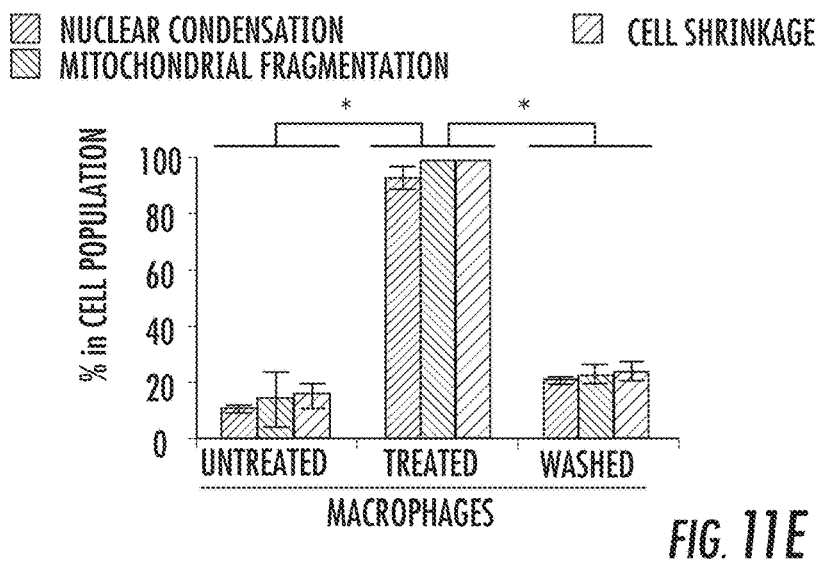

Cleavage and activation of caspase-3 is a biochemical hallmark of execution-stage apoptosis (Riedl and Shi, 2004; Taylor et al., 2008; Kroemer et al., 2009). Western blotting revealed an increase in cleaved caspase-3 and a decrease in full-length caspase-3 in both liver cells induced with ethanol and NIH 3T3 cells induced with DMSO (FIG. 10E). Of importance, after washing and then culturing of the apoptotic cells in fresh medium for 24 h, both full-length and cleaved caspase returned to pretreatment levels (FIG. 10E). Time-lapse live imaging of HeLa cells expressing a caspase biosensor confirmed that dying cells could reverse apoptosis, even after executioner caspase activation (FIGS. 10, F and G). The biosensor (NES-DEVD-YFP-NLS) is a protein composed of a nuclear exclusion signal (NES), a caspase-cleavable linker peptide (DEVD), which is the preferred cleavage site for caspase-3 (Talanian et al., 1997; Takemoto et al., 2003), yellow fluorescent protein (YFP), and a nuclear localization signal (NLS). In healthy cells, YFP is kept in the cytosol by the NES (FIG. 10F). On caspase activation, however the peptide is cleaved and the YFP is free to translocate to nucleus due to the NLS. As expected, the majority of YFP localized in the cytosol at the untreated cells (FIG. 10Gi). When exposed to 4.3% ethanol for 3 h, the vast majority of cells exhibited morphological hallmarks of apoptosis, including nuclear condensation, membrane blebbing, and cell shrinkage (FIG. 10G, ii and iii). YFP translocated to the nucleus, where it accumulated in many cells, whereas in others it appeared to be degraded. Of interest, after removal of the apoptotic inducer, the same cells regained normal morphology within 2 h (FIG. 10G, iv-vi). This indicates that single cells can reverse apoptosis after caspase activation. After removal of the inducer, >90% of cells recovered normal morphology, and 32% of them retained nuclear YFP (FIG. 10H). Taken together, our results indicate that cells can reverse apoptosis even after executioner caspase activation.

Reversal of apoptosis also occurred in primary rat heart cells exposed to 4.5% ethanol for 5 h, in *Mustela putoris furo* (Mpf) brain cells (CRL1516) exposed to 2 µM jasplakinolide for 50 h (FIG. 11, A-C), and in primary mouse macrophages exposed to 1 µM cucurbitacin I for 24 h (FIGS. 11, D and E). Greater than 90% of each cell type displayed morphological hallmarks of apoptosis, including nuclear condensation, mitochondrial fragmentation, and cell shrinkage. After removal of the inducer for 24 h, ~90% of the cells recovered morphology. Fluorescently labeled annexin V was also used to track reversal of apoptosis in heart and brain cells (FIG. 11A). Annexin V binds efficiently to phosphatidylserine, which moves from the inner to the outer leaflet of the plasma membrane during apoptosis (Logue et al., 2009). Ten minutes before washing, fluorescein isothiocyanate-conjugated annexin V (annexin V-FITC) was applied to label apoptotic cells (FIG. 11B), and >90% of both cell types were labeled (FIGS. 11, B and C). After removal of the inducer for 2 h to heart and 3 h to brain cells, >20% of heart cells and 60% of brain cells retained the annexin V-FITC label after morphological recovery (FIGS. 11, B and C). This provides an additional strategy to track cells that undergo apoptosis and survive, without the need of transfection.

Example 7: Cells can Reverse Apoptosis after DNA Damage has Occurred

Genomic destruction is a hallmark of apoptosis (Kerr et al., 1972; Taylor et al., 2008), raising the interesting possibility that cells that reverse apoptosis might acquire genetic alterations. During apoptotic induction, nuclear translocation of mitochondrial AIF and EndoG (FIGS. 12, A and B), which are apoptotic nucleases (Susin et al., 1999; Li et al., 2001), occurred in both liver and NIH 3T3 cells, suggesting that DNA was likely to be damaged.

Figure 12E:
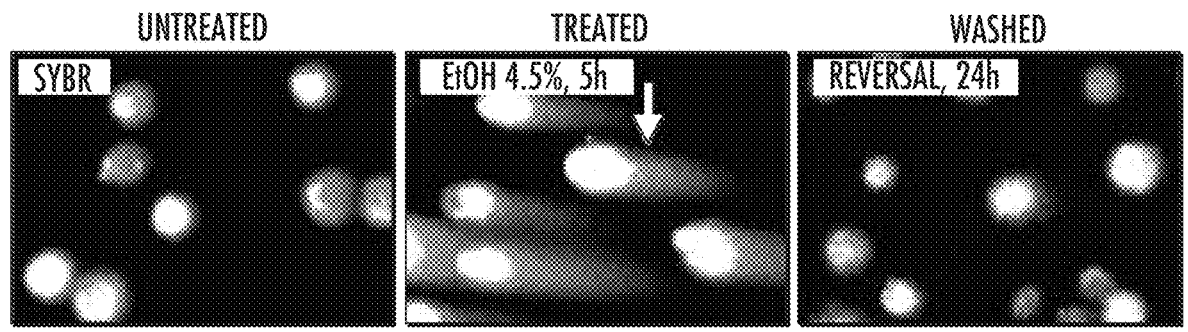
Figure 12F:
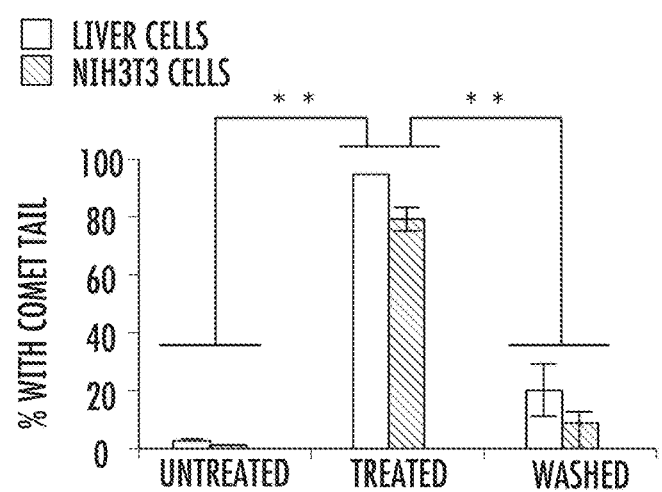
Figure 12G:
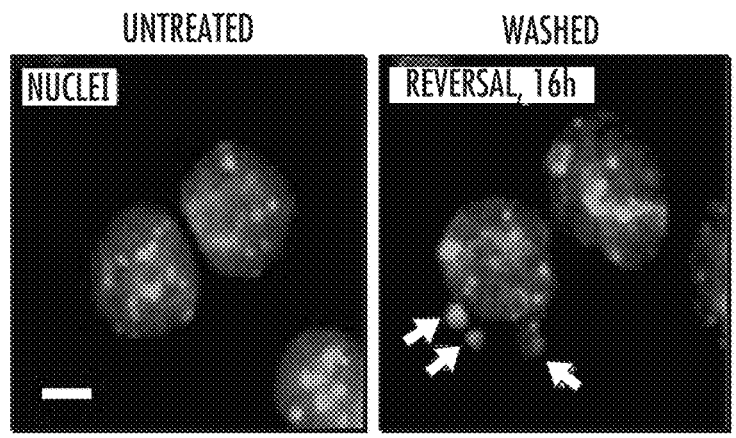

We also detected caspase-mediated damage of DNA repair systems. For example, the enzyme poly(ADP)-ribose polymerase-1 (PARP), which is required for genomic stability (Lazebnik et al., 1994; Wang et al., 1997), was cleaved in the induced cell population (FIG. 12C). Activated caspases also unlock DNA fragmentation factor/caspase-activated DNase (DFF40/CAD) by cleaving its inhibitor DFF45/ICAD (FIG. 12D; Liu et al., 1997; Enari et al., 1998). Thus mitochondria- and caspase-mediated DNA damage mechanisms were activated in the dying cells before washing.

The single-cell gel electrophoresis (comet) assay is a sensitive method for detecting DNA damage, including single- and double-strand breaks (Olive and Banath, 2006). The vast majority of both liver and NIH 3T3 cells treated with apoptotic inducers showed prominent comet tails before washing (FIGS. 12, E and F). After removal of the apoptotic inducers, the comet tails disappeared from most cells, indicating repair of the broken DNA (FIGS. 12, E and F). In addition, nuclear AIF and EndoG were reduced (FIGS. 12, A and B), and both full-length and cleaved PARP and ICAD returned to pretreatment levels (FIGS. 12, C and D). Taken together, these results indicate that cells can reverse the dying process even after DNA damage.

Figure 12H:
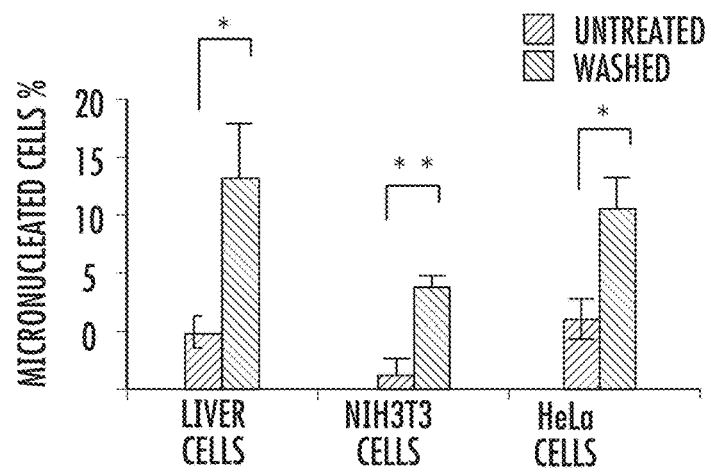
Figure 12I:
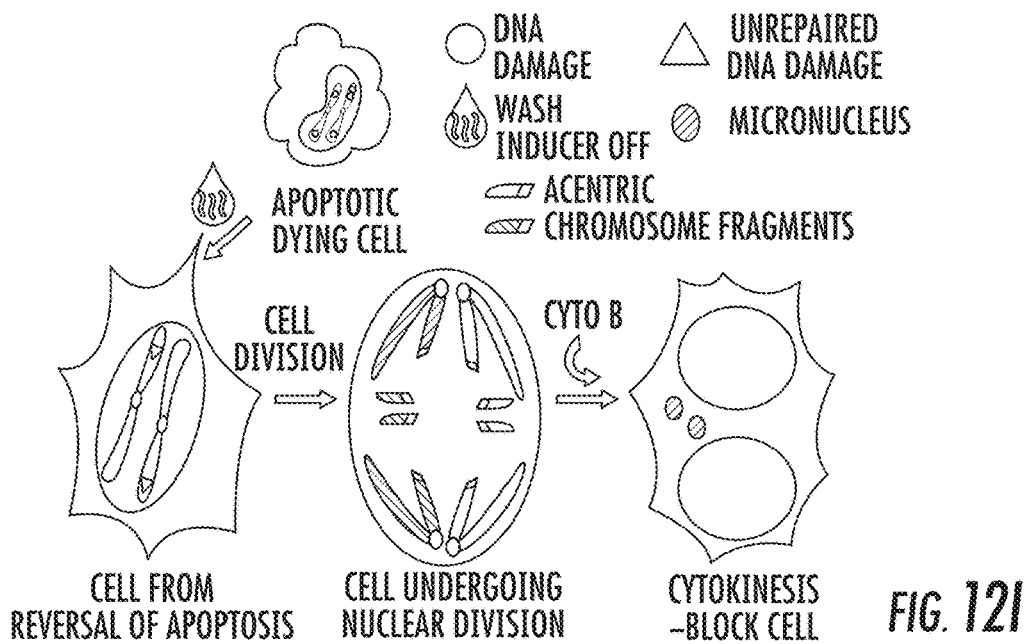
Figure 12J:
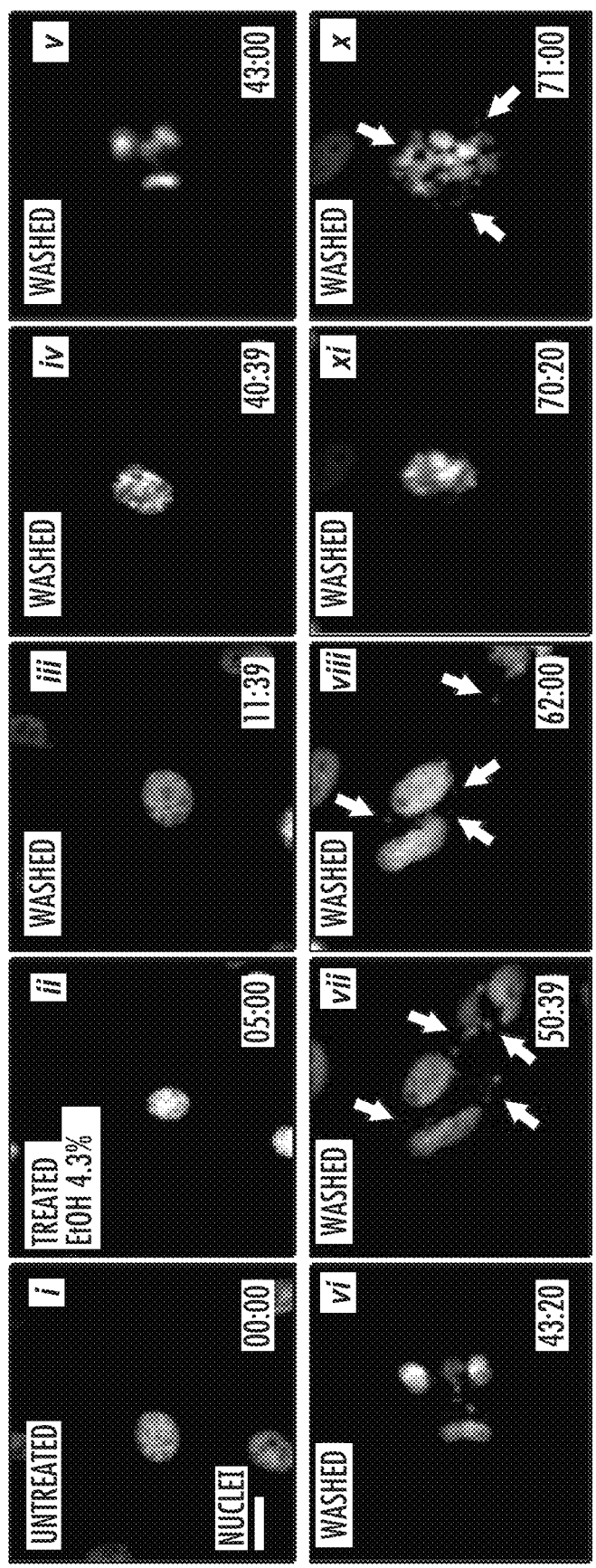
Figure 13E:
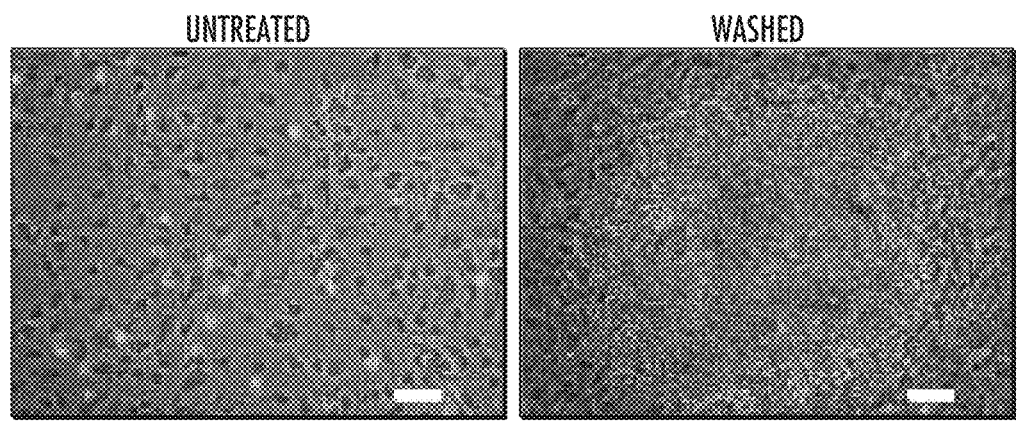
Figure 13G:
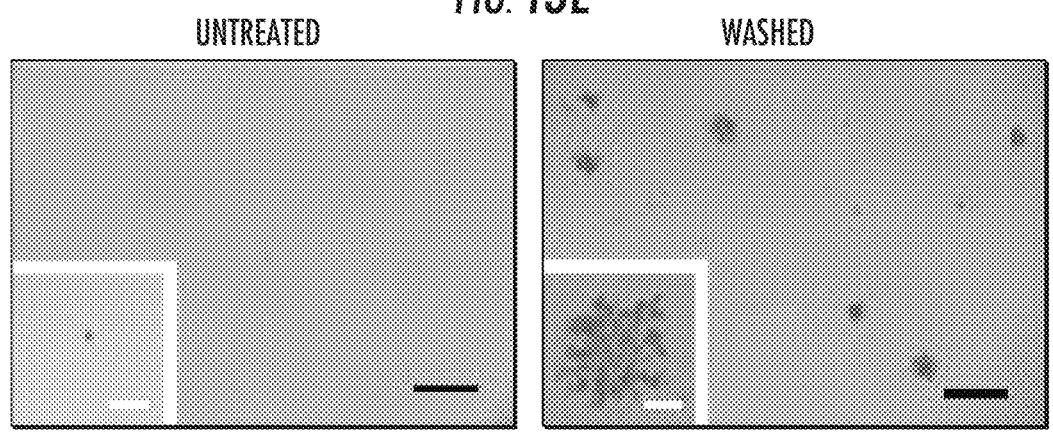
Figure 13F:
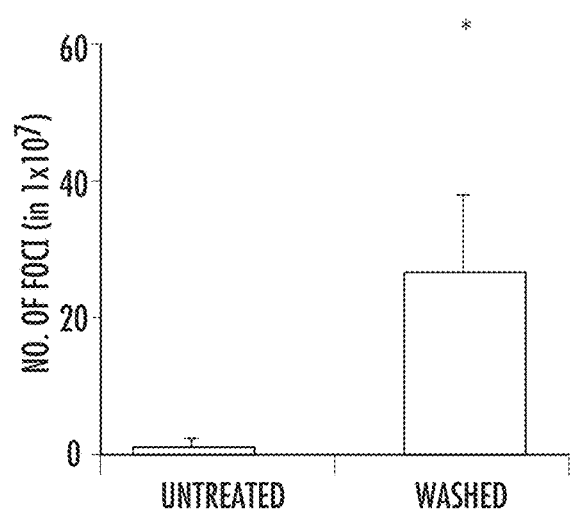
Figure 13H:
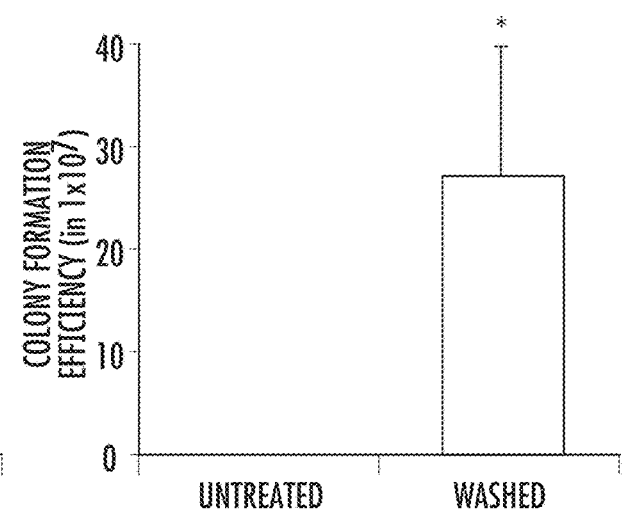

Example 8: Genetic Alterations and Transformation Occur after Reversal of Apoptosis To address how completely the DNA damage could be repaired, we performed cytokinesis-block micronucleus assays. At 16 h after removal of the inducer of apoptosis, although most nuclei appeared normal, there was a significant increase in the number of cells that displayed micronuclei compared with untreated controls in both liver and NIH 3T3 cells (FIGS. 12, G and H). Micronuclei are biomarkers of DNA damage, including chromosome breakage and/or whole chromosome loss in dividing cells (Fenech, 2007). The formation of micronuclei is evidence of unrepaired DNA damage (FIG. 12I), indicating that whereas many breaks were repaired, some remained. Increased in formation of micronuclei also occurred after reversal of ethanol-induced apoptosis in HeLa cells (FIG. 12H). Time-lapse live-cell microscopy revealed abnormalities, including formation of micronuclei during the first cell division after reversal of apoptosis (FIG. 12J, i-vii). Of note, new micronuclei formed during the division of the daughter cells (FIG. 12J, viii-x), suggesting that some DNA damage persisted.

The presence of unrepaired DNA damage in cells after reversal of apoptosis raised the question of whether surviving cells bear chromosomal abnormalities. Therefore we performed karyotyping on colchicine-treated, metaphase-arrested cells 3 d after induction and washing. We found a significant increase, compared with untreated cells, in chromosomal aberrations, including variations in chromosome number (FIGS. 13, A and B) and radial configurations (FIGS. 13, C and D), the latter of which result from misjoining of broken chromatids (German, 1964). This indicates the presence of genetic alterations in cells after reversal of apoptosis.

Genetic alterations in individual cells can promote phenotypic diversity (Bloom, 1972; Stratton et al., 2009) and can lead to transformation (Bloom, 1972; Rubin, 2008; Gordon et al., 2012), for which NIH 3T3 cells serve as an important experimental model (Rubin, 2008). A fraction of cells that reversed apoptosis displayed classic transformed phenotypes (Bloom, 1972; Cifone and Fidler, 1980; Rubin, 2008), including focus formation (FIGS. 13, E and F) and proliferation in soft agar (FIGS. 13, G and H), indicating loss of contact inhibition of growth and anchorage-independent growth, respectively. In contrast, similar phenotypes were virtually undetectable in untreated control cells. These phenotypes are also hallmarks of cancer cells (Bloom, 1972; Cifone and Fidler, 1980; Rubin, 2008), suggesting that reversal of apoptosis may be carcinogenic.

Example 9: New Transcription is Critical to Reverse Apoptosis

To gain insight into the mechanism by which cells reverse apoptosis and survive, we first tested whether new transcription is required. We detected new RNA synthesis immediately after removal of the apoptotic inducers (FIG. 14A), suggesting that new transcription occurs. We then exposed cells transiently to the reversible transcription inhibitor actinomycin D (Sawicki and Godman, 1972). This promoted persistence of cleaved caspase-3 (FIG. 14B) and irreversible cell death (FIG. 14C) as indicated by trypan blue staining, which labels dead cells due to their plasma membrane permeability (Kroemer et al., 2009). In contrast, the same concentration of actinomycin D did not cause significant cell death in control cells that had not been treated with apoptotic inducers (FIGS. 14, B and C). These results indicate that new transcription is required for the reversal of apoptosis.

Example 10: Prosurvival Factors Contribute to Reversal of Apoptosis

Figure 14A:
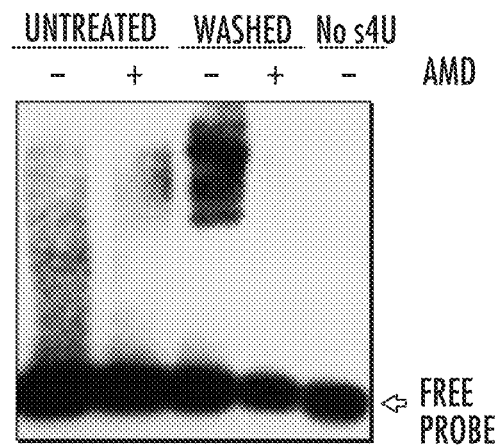
FIG. 14A-14F: Critical contributing factors in reversal of apoptosis.
Figure 14B:
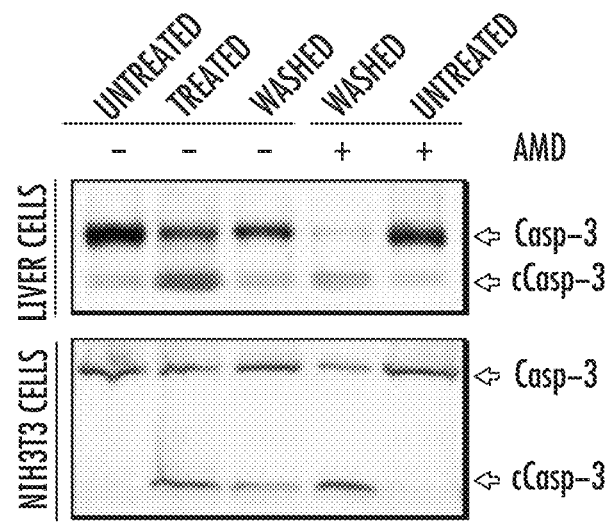
Figure 14C:
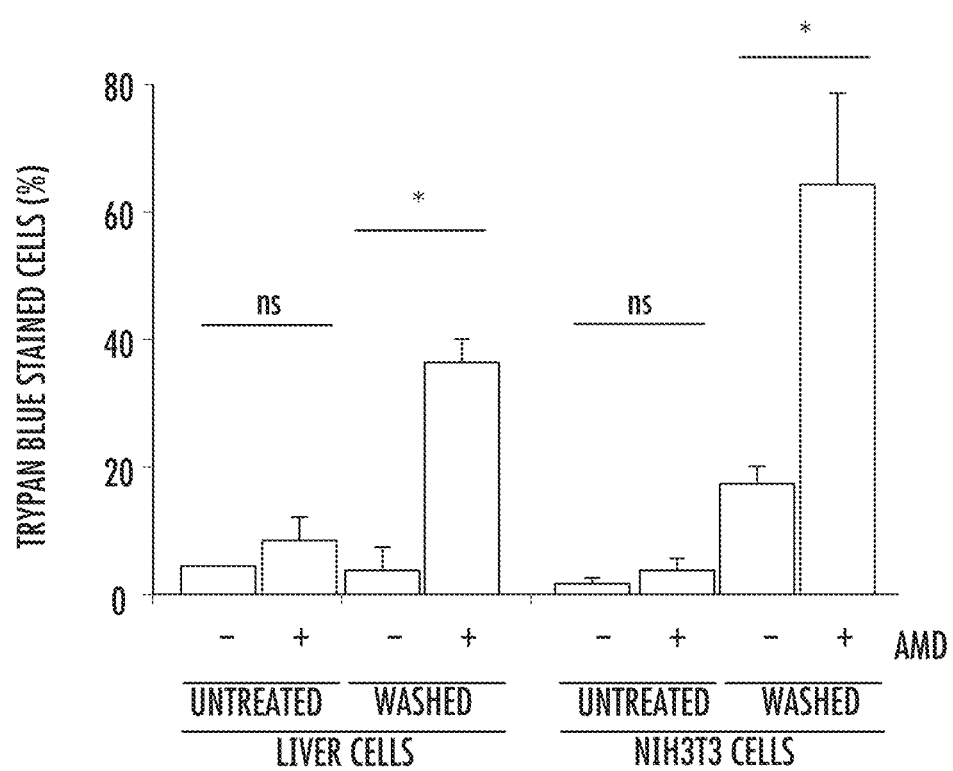
Figure 14D:
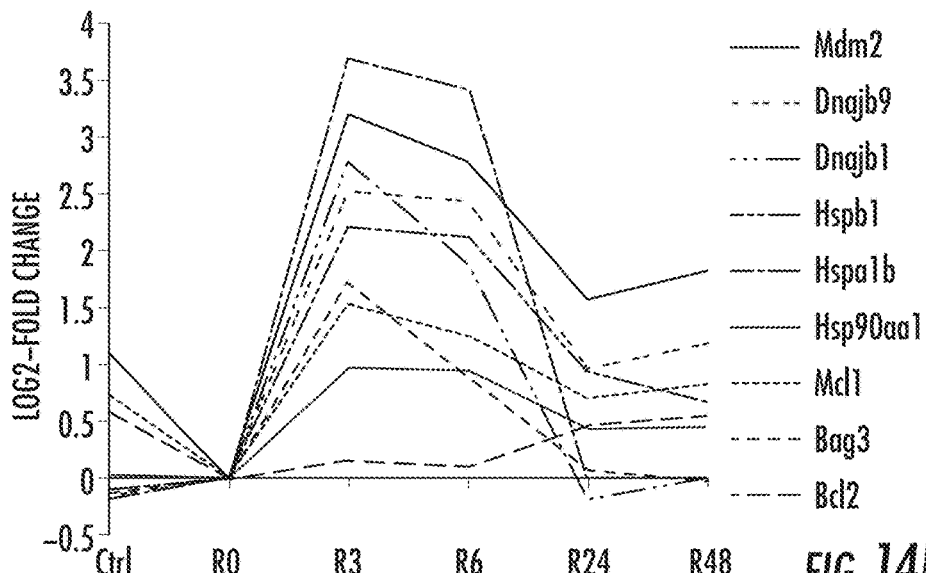
Figure 14E:
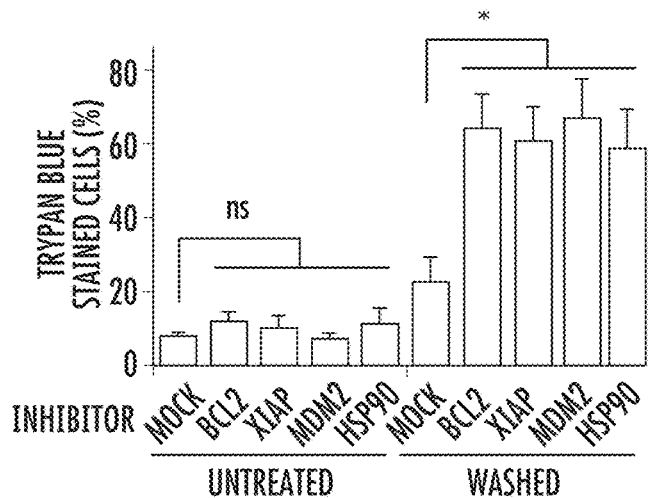

To determine the transcriptional profiles of liver cells undergoing reversal of apoptosis, we conducted time-course gene expression analysis of 30,774 transcripts using RNA microarrays and quantitative PCR with reverse transcription (qRT-PCR). We observed enhanced expression of multiple prosurvival genes, including antiapoptotic BCL-2 family members (Bag3, Bcl2, and Mcl1), X-linked inhibitor of apoptosis protein (XIAP), the murine double minute (MDM2), and heat shock proteins (Dnajb1, Dnajb9, Hsp90aa1, Hspa1b, and Hspb1), after removal of the apoptotic inducer (FIG. 14D). Expression of most of these genes peaked at the 3- and 6-h time points after removal of the apoptotic inducer and then dropped again.

Figure 14F:
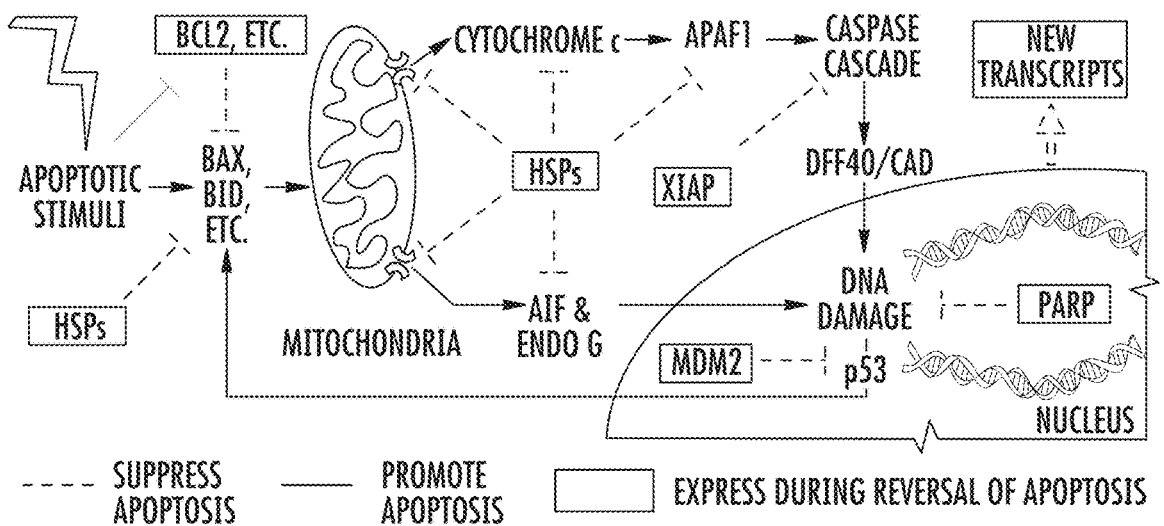

The contributions of some of the identified candidates to reversing apoptosis were tested by application of pharmacological inhibitors to liver cells after removal of the apoptotic stimuli. Inhibition of BCL-2, XIAP, MDM2, or HSP90 significantly suppressed reversal of apoptosis, as indicated by the increased percentage of trypan blue-stained cells (FIG. 14E) and persistence of cleaved caspase-3 (data not shown), suggesting their roles in reversing apoptosis by suppressing activated proapoptotic pathways (FIG. 14F).

Supplemental figures, movies and information can be found at http://www.molbiolcell. org/content/23/12/2240/suppl/DC1.

REFERENCES

1. Aitken R J, Findlay J K, Hutt K J, Kerr J B (2011). Apoptosis in the germ line. Reproduction 141, 139-150.
2. Arama E, Agapite J, Steller H (2003). Caspase activity and a specific cytochrome C are required for sperm differentiation in *Drosophila*. Dev Cell 4, 687-697.
3. Bloom A D (1972). Induced chromosomal aberrations: biological and clinical significance. J Pediatr 81, 1-8.
4. Boffetta P, Hashibe M (2006). Alcohol and cancer. Lancet Oncol 7, 149-156.
5. Capy P, Gasperi G, Biemont C, Bazin C (2000). Stress and transposable elements: co-evolution or useful parasites? Heredity 85, 101-106.
6. Chabaud S, Moulin V J (2011). Apoptosis modulation as a promising target for treatment of systemic sclerosis. Int J Rheumatol 2011, 495792.
7. Chipuk J E, Moldoveanu T, Llambi F, Parsons M J, Green D R (2010). The BCL-2 family reunion. Mol Cell 37, 299-310.
8. Cifone M A, Fidler I J (1980). Correlation of patterns of anchorage-independent growth with in vivo behavior of cells from a murine fibrosarcoma. Proc Natl Acad Sci USA 77, 1039-1043.
9. Coleman M L, Sahai E A, Yeo M, Bosch M, Dewar A, Olson M F (2001). Membrane blebbing during apoptosis results from caspase-mediated activation of ROCK I. Nat Cell Biol 3, 339-345.
10. Drummond-Barbosa D, Spradling A C (2001). Stem cells and their progeny respond to nutritional changes during *Drosophila* oogenesis. Dev Biol 231, 265-278.
11. Enari M, Sakahira H, Yokoyama H, Okawa K, Iwamatsu A, Nagata S (1998). A caspase-activated DNase that degrades DNA during apoptosis, and its inhibitor ICAD. Nature 391, 43-50.
12. Fenech M (2007). Cytokinesis-block micronucleus cytome assay. Nat Protoc 2, 1084-1104.
13. Fischer U, Schulze-Osthoff K (2005). Apoptosis-based therapies and drug targets. Cell Death Differ 12(Suppl 1), 942-961.
14. Fu D, Calvo J A, Samson L D (2012). Balancing repair and tolerance of DNA damage caused by alkylating agents. Nat Rev Cancer 12, 104-120.
15. Fuchs Y, Steller H (2011). Programmed cell death in animal development and disease. Cell 147, 742-758.
16. German J (1964). Cytological evidence for crossing-over in vitro in human lymphoid cells. Science 144, 298-301.
17. Goldin R D, Hunt N C, Clark J, Wickramasinghe S N (1993). Apoptotic bodies in a murine model of alcoholic liver disease: reversibility of ethanol-induced changes. J Pathol 171, 73-76.
18. Gordon D J, Resio B, Pellman D (2012). Causes and consequences of aneuploidy in cancer. Nat Rev Genet 13, 189-203.
19. Gordon W C, Casey D M, Lukiw W J, Bazan N G (2002). DNA damage and repair in light-induced photoreceptor degeneration. Invest Ophthalmol Visual Sci 43, 3511-3521.
20. Green D R, Kroemer G (2004). The pathophysiology of mitochondrial cell death. Science 305, 626-629.
21. Guicciardi M E, Gores G J (2010). Apoptosis as a mechanism for liver disease progression. Semin Liver Dis 30, 402-410.
22. Hu S, Wu Z, Yang L, Fung M C (2009). Molecular cloning and expression of a functional anti-inflammatory protein, Sj16, of *Schistosoma japonicum*. Int J Parasitol 39, 191-200.
23. Iravanian S, Nabutovsky Y, Kong C R, Saha S, Bursac N, Tung L (2003). Functional reentry in cultured monolayers of neonatal rat cardiac cells. Am J Physiol Heart Circ Physiol 285, H449-H456.
24. Jacobson M D, Weil M, Raff M C (1997). Programmed cell death in animal development. Cell 88, 347-354.
25. Jaiswal J K, Mattoussi H, Mauro J M, Simon S M (2003). Long-term multiple color imaging of live cells using Quantum Dot bioconjugates. Nat Biotechnol 21, 47-51.

26. Jiang N, Bao Z, Zhang X, Hirochika H, Eddy S R, McCouch S R, Wessler S R (2003). An active DNA transposon family in rice. Nature 421, 163-167.
27. Johnstone R W, Ruefli A A, Lowe S W (2002). Apoptosis: a link between cancer genetics and chemotherapy. Cell 108, 153-164.
28. Kerr J F, Wyllie A H, Currie A R (1972). Apoptosis: a basic biological phenomenon with wide-ranging implications in tissue kinetics. Br J Cancer 26, 239-257.
29. Kroemer G et al. (2009). Classification of cell death: recommendations of the Nomenclature Committee on Cell Death 2009. Cell Death Differ 16, 3-11.
30. Lazebnik Y A, Kaufmann S H, Desnoyers S, Poirier G G, Earnshaw W C (1994). Cleavage of poly(ADP-ribose) polymerase by a proteinase with properties like ICE. Nature 371, 346-347.
31. Li L Y, Luo X, Wang X (2001). Endonuclease G is an apoptotic DNase when released from mitochondria. Nature 412, 95-99.
32. Liu P et al. (2011). Chromosome catastrophes involve replication mechanisms generating complex genomic rearrangements. Cell 146, 889-903.
33. Liu X, Zou H, Slaughter C, Wang X (1997). DFF, a heterodimeric protein that functions downstream of caspase-3 to trigger DNA fragmentation during apoptosis. Cell 89, 175-184.
34. Logue S E, Elgendy M, Martin S J (2009). Expression, purification and use of recombinant annexin V for the detection of apoptotic cells. Nat Protoc 4, 1383-1395.
35. Luthi A U, Martin S J (2007). The CASBAH: a searchable database of caspase substrates. Cell Death Differ 14, 641-650.
36. MacLeod R A, Kaufmann M, Drexler H G (2007). Cytogenetic harvesting of commonly used tumor cell lines. Nat Protoc 2, 372-382.
37. Masters J R (2002). HeLa cells 50 years on: the good, the bad and the ugly. Nat Rev Cancer 2, 315-319.
38. McClintock B (1984). The significance of responses of the genome to challenge. Science 226, 792-801.
39. McKechnie N M, Foulds W S (1980). Recovery of the rabbit retina after light damage (preliminary observations). Albrecht Von Graefes Arch Klin Exp Ophthalmol 212, 271-283.
40. McKillop I H, Schrum L W (2005). Alcohol and liver cancer. Alcohol 35, 195-203.
41. Milligan S C, Alb J G Jr, Elagina R B, Bankaitis V A, Hyde D R (1997). The phosphatidylinositol transfer protein domain of *Drosophila* retinal degeneration B protein is essential for photoreceptor cell survival and recovery from light stimulation. J Cell Biol 139, 351-363.
42. Narula J, Haider N, Arbustini E, Chandrashekhar Y (2006). Mechanisms of disease: apoptosis in heart failure-seeing hope in death. Nat Clin Pract Cardiovasc Med 3, 681-688.
43. Narula J et al. (1999). Apoptosis in heart failure: release of cytochrome c from mitochondria and activation of caspase-3 in human cardiomyopathy. Proc Natl Acad Sci USA 96, 8144-8149.
44. Olive P L, Banath J P (2006). The comet assay: a method to measure DNA damage in individual cells. Nat Protoc 1, 23-29.
45. Reed J C, Paternostro G (1999). Postmitochondrial regulation of apoptosis during heart failure. Proc Natl Acad Sci USA 96, 7614-7616.
46. Riedl S J, Shi Y (2004). Molecular mechanisms of caspase regulation during apoptosis. Nat Rev Mol Cell Biol 5, 897-907.
47. Rosenberg S M (2001). Evolving responsively: adaptive mutation. Nat Rev Genet 2, 504-515.
48. Ross G M (1999). Induction of cell death by radiotherapy. Endocr Related Cancer 6, 41-44.
49. Rubin H (2008). Cell-cell contact interactions conditionally determine suppression and selection of the neoplastic phenotype. Proc Natl Acad Sci USA 105, 6215-6221.
50. Salinas L S, Maldonado E, Navarro R E (2006). Stress-induced germ cell apoptosis by a p53 independent pathway in *Caenorhabditis elegans*. Cell Death Differ 13, 2129-2139.
51. Sawicki S G, Godman G C (1972). On the recovery of transcription after inhibition by actinomycin D. J Cell Biol 55, 299-309.
52. Stephens P J et al. (2011). Massive genomic rearrangement acquired in a single catastrophic event during cancer development. Cell 144, 27-40.
53. Stratton M R, Campbell P J, Futreal P A (2009). The cancer genome. Nature 458, 719-724.
54. Susin S A et al. (1999). Molecular characterization of mitochondrial apoptosis-inducing factor. Nature 397, 441-446.
55. Takemoto K, Nagai T, Miyawaki A, Miura M (2003). Spatio-temporal activation of caspase revealed by indicator that is insensitive to environmental effects. J Cell Biol 160, 235-243.
56. Talanian R V, Quinlan C, Trautz S, Hackett M C, Mankovich J A, Banach D, Ghayur T, Brady K D, Wong W W (1997). Substrate specificities of caspase family proteases. J Biol Chem 272, 9677-9682.
57. Tang H L, Yuen K L, Tang H M, Fung M C (2009). Reversibility of apoptosis in cancer cells. Br J Cancer 100, 118-122.
58. Taylor R C, Cullen S P, Martin S J (2008). Apoptosis: controlled demolition at the cellular level. Nat Rev Mol Cell Biol 9, 231-241.
59. Wang Z Q, Stingl L, Morrison C, Jantsch M, Los M, Schulze-Osthoff K, Wagner E F (1997). PARP is important for genomic stability but dispensable in apoptosis. Genes Dev 11, 2347-2358.
60. Zeiner G M, Cleary M D, Fouts A E, Meiring C D, Mocarski E S, Boothroyd J C (2008). RNA analysis by biosynthetic tagging using 4-thiouracil and uracil phosphoribosyltransferase. Methods Mol Biol 419, 135-146.
61. Zurlo J, Arterburn L M (1996). Characterization of a primary hepatocyte culture system for toxicological studies. In Vitro Cell Dev Biol Anim 32, 211-220.

We claim:

1. A method for identifying cells that survive apoptosis via anastasis comprising the steps of:
   a. transiently inducing apoptosis in a cell comprising an anastasis biosensor, wherein the anastasis biosensor comprises:
      (i) a transcription factor complex comprising a Gal4 transcription factor linked to a transmembrane domain via a caspase enzyme cleavable linker, wherein the transcription factor complex is tethered to the plasma membrane of the cell in which the in vivo anastasis biosensor is expressed, and wherein the caspase enzyme is specifically expressed during apoptosis, and
      (ii) a reporter system comprising (1) a first nucleic acid encoding flippase operably linked to the upstream activating sequence that binds Gal4; and (2) a second nucleic acid comprising a flippase recognition target (FRT)-flanked stop codon cassette separating a constitutive promoter and a fluorescent protein open reading frame,
   b. detecting fluorescent protein expression, wherein a cell expressing the in vivo anastasis biosensor that survives apoptosis via anastasis expresses the fluorescent protein.

2. The method of claim 1, wherein the fluorescent protein comprises green fluorescent protein, red fluorescent protein, or yellow fluorescent protein.

* * * * *